(12) United States Patent
Tekeste

(10) Patent No.: US 11,517,675 B2
(45) Date of Patent: Dec. 6, 2022

(54) MEDICAL DEVICES FOR BLOOD REFLUX PREVENTION AND METHODS OF USE

(71) Applicant: Becton, Dickinson and Company, Franklin Lakes, NJ (US)

(72) Inventor: Girum Yemane Tekeste, Hackensack, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1108 days.

(21) Appl. No.: 16/141,169

(22) Filed: Sep. 25, 2018

(65) Prior Publication Data
US 2019/0022324 A1  Jan. 24, 2019

Related U.S. Application Data

(63) Continuation of application No. 15/066,136, filed on Mar. 10, 2016, now Pat. No. 10,086,142, which is a continuation of application No. 13/589,679, filed on Aug. 20, 2012, now Pat. No. 9,302,049.

(51) Int. Cl.
*A61M 5/31* (2006.01)
*A61M 39/24* (2006.01)

(52) U.S. Cl.
CPC .............. *A61M 5/31* (2013.01); *A61M 39/24* (2013.01); *A61M 2005/3104* (2013.01); *A61M 2005/3117* (2013.01); *A61M 2005/3128* (2013.01); *A61M 2039/2406* (2013.01); *A61M 2039/2433* (2013.01)

(58) Field of Classification Search
CPC ............ A61M 2005/3118; A61M 5/31; A61M 2005/3104; A61M 2005/3117; A61M 39/162; A61M 39/165
See application file for complete search history.

(56) References Cited

U.S. PATENT DOCUMENTS

| 1,712,070 A | 5/1929 | Cressler |
| 2,693,803 A | 11/1954 | Ogle |
| 2,893,390 A * | 7/1959 | Lockhart ............... A61M 5/286 |
| | | 604/238 |
| 4,466,446 A | 8/1984 | Baidwan et al. |
| 4,752,290 A | 6/1988 | Schramm |

(Continued)

FOREIGN PATENT DOCUMENTS

| AU | 560426 B2 | 4/1987 |
| CN | 203539803 U | 4/2014 |

(Continued)

OTHER PUBLICATIONS

"http://www.fda.gov/MEDICALDEVICES/SAFETY/ ALERTSANDNOTICES/UCM220459.HTM", U.S. Food and Drug Administration, Letter to Infection Control Practitioners, Nov. 13, 2015, 4 pages.

(Continued)

*Primary Examiner* — Bradley J Osinski
(74) *Attorney, Agent, or Firm* — Servilla Whitney LLC

(57) ABSTRACT

Described is a catheter patency maintenance device comprising of a flush syringe, an elongate plunger rod with a stopper slidably positioned within the barrel, a cap, disinfectant and a valve movable between an open position and a closed position. The valve may include a valve stem and/or openings in the valve to permit fluid flow. Methods of using the flush syringe assemblies are also described.

17 Claims, 28 Drawing Sheets

(56) References Cited

U.S. PATENT DOCUMENTS

| | | | |
|---|---|---|---|
| 4,927,417 A * | 5/1990 | Moncada | A61M 5/3271 604/263 |
| 5,342,320 A | 8/1994 | Cameron | |
| 6,190,364 B1 | 2/2001 | Imbert | |
| 8,172,813 B2 | 5/2012 | Janish | |
| 2001/0029355 A1 | 10/2001 | Szames et al. | |
| 2005/0015055 A1 | 1/2005 | Yang | |
| 2005/0154353 A1 | 7/2005 | Alheidt | |
| 2008/0300551 A1 | 12/2008 | Schiller et al. | |
| 2009/0247958 A1 | 10/2009 | Carlyon | |
| 2009/0247961 A1 | 10/2009 | Carlyon | |
| 2010/0010056 A1 | 1/2010 | Rehan et al. | |
| 2011/0054440 A1 | 3/2011 | Lewis | |
| 2011/0275988 A1 | 11/2011 | Davis et al. | |
| 2012/0016318 A1 | 1/2012 | Hoang et al. | |
| 2012/0095679 A1 | 7/2012 | Hawasheen | |
| 2014/0052074 A1 | 2/2014 | Tekeste | |

FOREIGN PATENT DOCUMENTS

| | | |
|---|---|---|
| JP | S5510186 A | 1/1980 |
| JP | S60175249 | 11/1985 |
| JP | H11503941 A | 4/1999 |
| JP | 2000097380 A | 4/2000 |
| JP | 2003505158 A | 2/2003 |
| JP | 2007513690 A | 5/2007 |
| JP | 2007537399 A | 12/2007 |
| JP | 2009537250 A | 10/2009 |
| WO | 2005011798 A1 | 9/2006 |
| WO | 2012060365 A1 | 5/2012 |
| WO | 2012/095679 A1 | 7/2012 |

OTHER PUBLICATIONS

PCT International Search Report and Written Opinion in PCT/US2013/055773, dated Jan. 29, 2014, 15 pages.

* cited by examiner

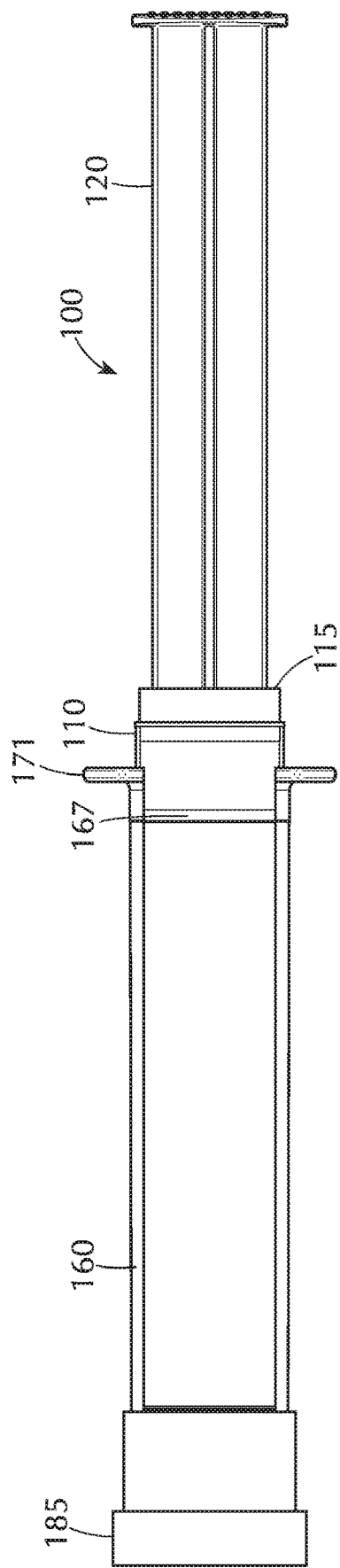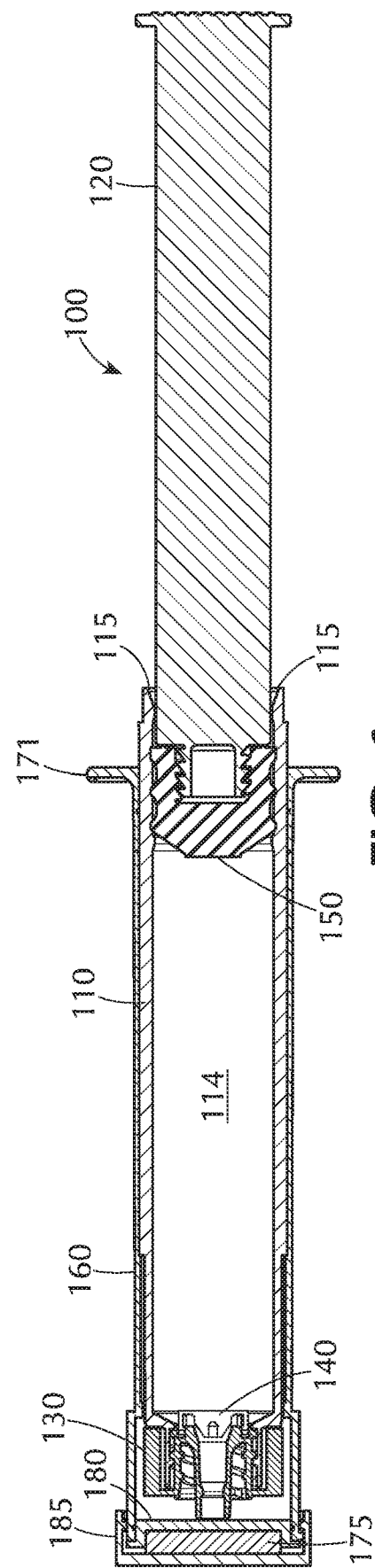

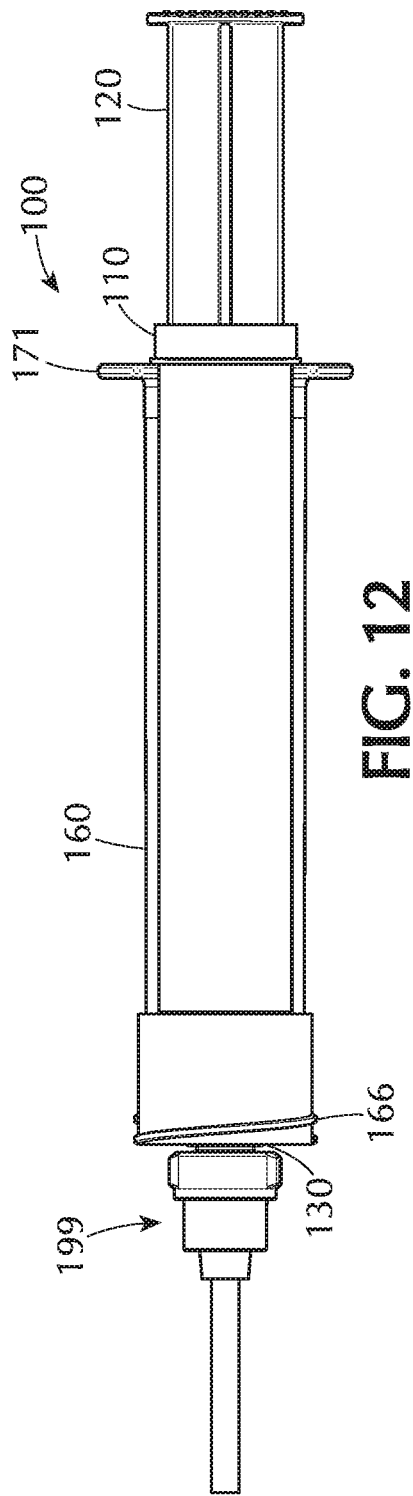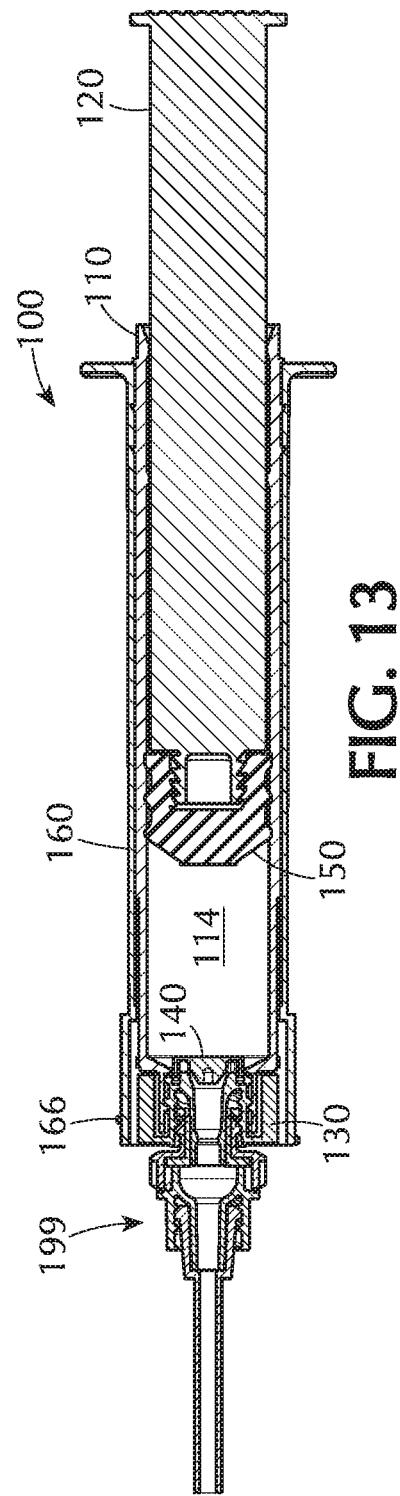

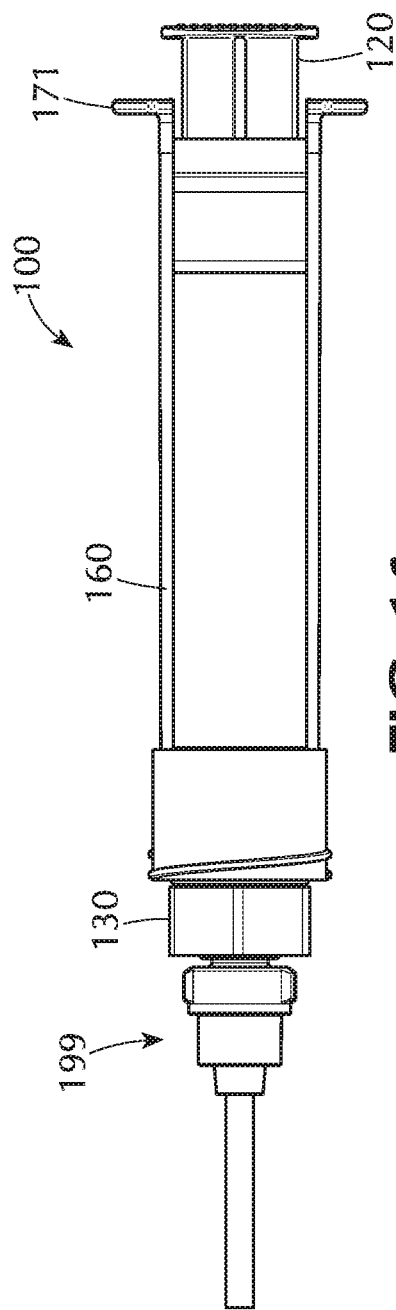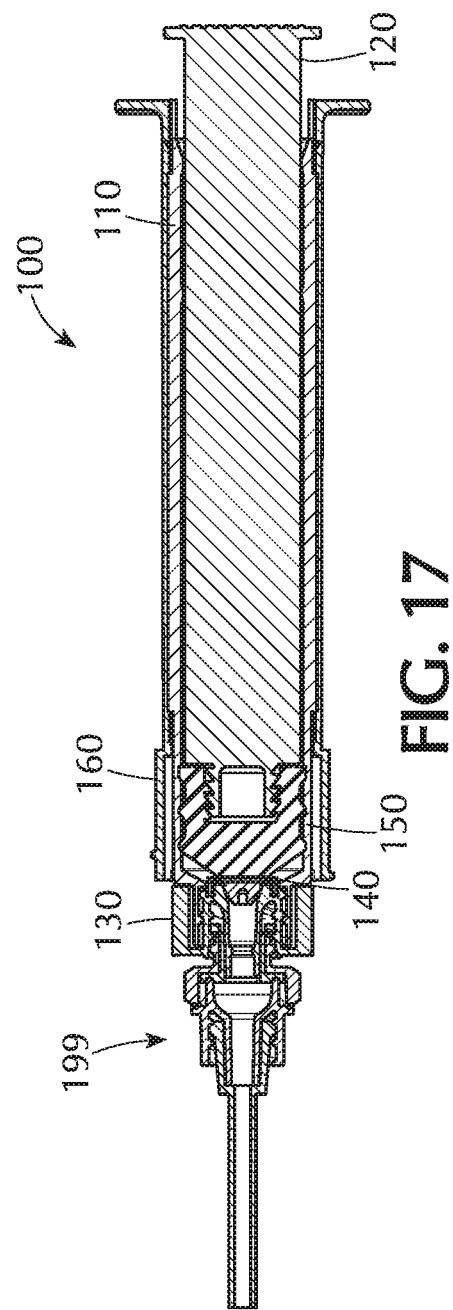
FIG. 16
FIG. 17

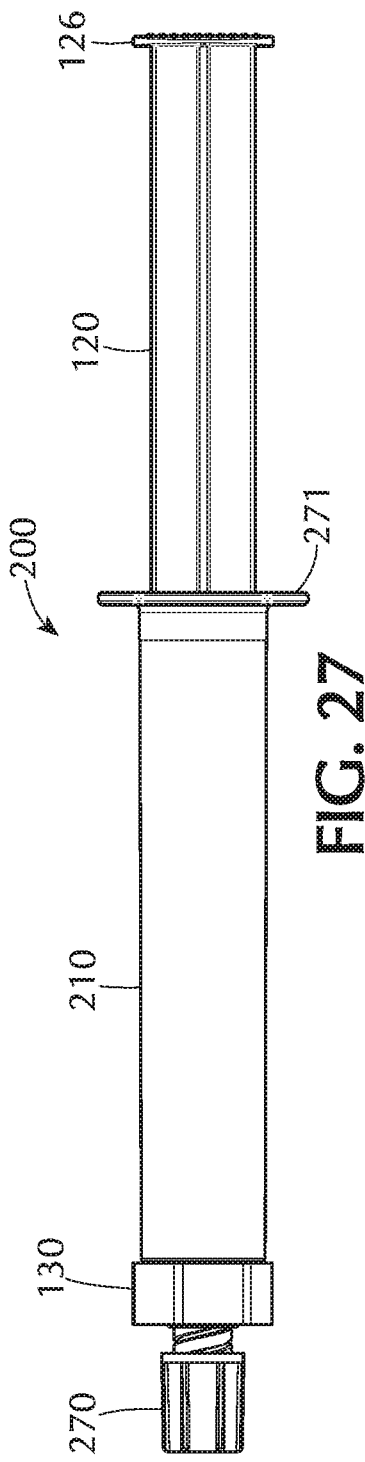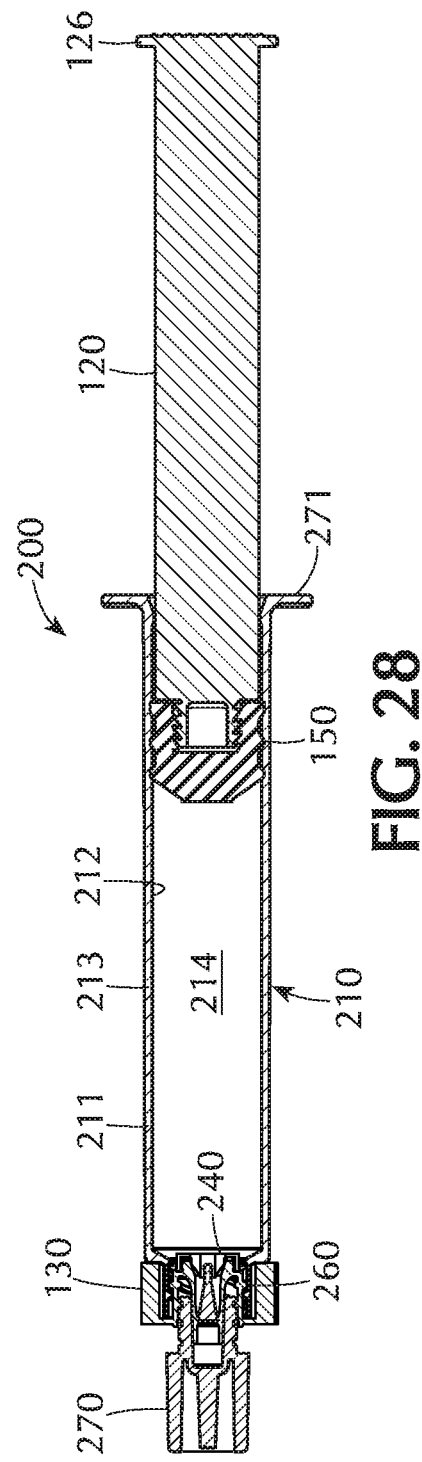

MEDICAL DEVICES FOR BLOOD REFLUX PREVENTION AND METHODS OF USE

CROSS-REFERENCE TO RELATED APPLICATIONS

This application is a continuation of U.S. patent application Ser. No. 15/066,136, filed Mar. 10, 2016 which issued on Oct. 2, 2018 as U.S. Pat. No. 10,086,142, which is a continuation of U.S. patent application Ser. No. 13/589,679, filed Aug. 20, 2012, which issued on Apr. 5, 2016 as U.S. Pat. No. 9,302,049, the entire disclosure of which is hereby incorporated by reference herein.

TECHNICAL FIELD

Embodiments of the invention generally relate to apparatus and methods to prevent blood reflux in vascular access devices (VAD). More specifically, embodiments of the invention are directed to technology to reduce the risk for bloodstream infections (CRBSI) and intravenous (IV) line patency maintenance including one or more of IV connectors cleaning, reflux prevention and connector capping technology.

BACKGROUND

Current technologies and procedures for preventing catheter related bloodstream infections are impractical, difficult and cumbersome to practice. Part of the current IV catheter patency maintenance procedure requires flushing the IV line with a pre-filled Saline (0.9% NaCl) syringe. If positive displacement connectors are not utilized blood can reflux back into the catheter and form a blood clot, which will occlude the IV line and block the catheter lumen. In addition, there are no automatic catheter connector capping systems, which are designed to protect the catheter connector after accessing the catheter and flushing the IV line.

Currently, when a connector is not being utilized, the inlet port surfaces are exposed to the environment. This allows microorganisms to populate the exposed connector inlet surfaces and enter the IV line during flushing; blood reflux can cause clot formation inside catheter lumens; microorganisms from the connector inlet surfaces can colonize blood clots inside the catheter lumens and then infect patients; and blood clots can occlude IV lines, making the lines difficult to use. In some patients, dislodged blood clots from catheter lumens could cause further complications. The recommended practices suggest cleaning the connector almost after every other step. This makes the IV maintenance process very cumbersome and it is rarely implemented.

One purpose of positive displacement valves (connectors) is to prevent blood reflux into catheters. When IV devices are being disconnected from the inlet port of valves/connectors, blood reflux can occur at the tip of the catheter. Positive displacement valves are used to prevent catheter occlusion from thrombosis or blood clot formation due to blood reflux. Some positive displacement valve manufacturers recommend saline only flushing (i.e., heparin lock flush is not needed since the valves prevent reflux). When blood is drawn through positive displacement valves, blood proteins adhere to the valve parts and can be colonized by microorganisms. The valve inlet port surfaces are potential sources for microorganisms. Positive displacement valves have mechanical parts with complex features. Therefore, it is difficult to clean the internal parts of valves by the flushing process. The FDA has raised concerns regarding CRBSI risks associated with positive displacement valves and ordered a study to address the risk. See http://www.fda.gov/MedicalDevices/Safety/AlertsandNotices/ucm220459.htm.

Additionally, microorganisms from the skin can populate unprotected connector inlet port surfaces. Microorganisms from the connector inlet surfaces can be infused into the blood stream with IV solutions (e.g., during flushing). Further issues with current procedures include, but are not limited to, blood clots that get colonized by microorganisms inside catheters, inadequate or inconvenient connector cleaning practices; and complex positive displacement valve/connector parts.

There are a number of issues with current IV line maintenance and IV drug delivery practices. When catheterized patients are discharged from treatment centers, the inlet port is of the connector is exposed to the environment, and it can be populated or colonized by microorganisms. The possibility of contaminating the connector exists outside of treatment centers. Clinicians need both of their hands to clean connectors. Clinicians also need both hands to uncap a flush syringe and connect it to an IV line connector. This means after cleaning the connector, clinicians can drop the connector back on to the skin to pick up a flush syringe (i.e. two hands are needed to uncap a flush syringe and connect it to a connector).

There are also a number of issues with current IV line maintenance and IV drug delivery practices. The possibility of contaminating the connector also exists, in the period between flushing the IV line and administering therapy. Blood reflux is not prevented, unless positive displacement valves are used.

Therefore, there is a need in the art for devices and methods to protect the connector inlet surfaces from contamination, protect the flush syringe luer tip from contamination and prevent reflux to avoid blood clot formation inside catheter lumens, make the connector cleaning process convenient, consistent and intuitive for clinicians and/or flush the connector and the catheter adequately.

SUMMARY

One or more embodiments are directed to systems, devices and methods that can be designed to prevent blood reflux, and cap the IV catheter connector after flushing the IV line.

Embodiments of the invention are directed to flush syringe assemblies comprising a barrel, an elongate plunger rod, a cap and a valve. The barrel includes a side wall having an inside surface defining a chamber for retaining fluid, and outside surface, an open proximal end and a distal end including a distal wall having an aperture therethrough in fluid communication with the chamber. The elongate plunger rod is disposed within the barrel. The plunger rod comprises a distal end including a stopper slidably positioned in fluid-tight contact with the inside surface of the barrel so that distal movement of the stopper relative to the barrel pushes fluid out of the barrel. The cap comprises a passageway therethrough in fluid communication with the chamber. The cap includes a Luer connector on a distal end and being releasably connectable to a vascular access device (VAD) and a proximal end releasably attachable to the barrel. The valve is positioned adjacent the distal end of the barrel and the proximal end of the cap. The valve is movable between an open position to permit fluid flow between the chamber and the VAD and a closed position to prevent fluid flow from a blood vessel to the VAD.

In some embodiments, the valve comprises a plug having a proximal face and a sidewall extending distally therefrom. The sidewall includes a plurality of openings that allow fluid communication between the chamber and the VAD. In one or more embodiments, when the plug is in the open position there is fluid communication between the chamber and the cap through the plurality of openings and when the plug is moved distally to the closed position, the chamber is isolated from the VAD.

In some embodiments, the plug is flexible. In one or more embodiments, the plug is made from an elastomeric material.

In some embodiments, the valve comprises a valve stem extending distally from a center of the valve. The valve stem has a proximal diameter and a distal diameter greater than the proximal diameter and the cap further comprises a valve seat that forms a fluid-tight seal when the valve stem is in complete contact therewith. In one or more embodiments, when distally directed force is applied to the stopper, the valve stem is not in complete contact with the valve seat and when a proximally directed force or no-force is applied to the stopper, the valve stem is in complete contact with the valve seat to form a fluid-tight seal isolating the chamber from the VAD.

In some embodiments, the valve comprises a proximal face and a sidewall extending distally therefrom, the proximal face comprising a plurality of openings allowing fluid communication between the chamber and the cap, and a valve stem extending distally from a center of the valve, the valve stem having a proximal diameter and a distal diameter greater than the proximal diameter and the cap further comprises a valve seat that forms a fluid-tight seal when the valve stem is in complete contact therewith. In one or more embodiments, when distally directed force is applied to the stopper, the valve stem is not in complete contact with the valve seat and when a proximally directed force or no-force is applied to the stopper, the valve stem is in complete contact with the valve seat to form a fluid-tight seal isolating the chamber from the VAD. In some embodiments, the sidewall of the valve includes a plurality of openings that allow fluid communication between the chamber and the cap.

In some embodiments, the valve comprises a proximal face and a sidewall extending distally therefrom. A plurality of openings in one or more of the proximal face and the sidewall allow fluid communication between the chamber and the cap. A valve stem extends distally from a center of the valve. The valve stem has a proximal end with a proximal diameter and a distal end with a distal diameter greater than the proximal diameter. The cap further comprises a valve seat within the passageway biased radially inwardly. The valve seat has a proximal face and a distal face and the distal end of the valve stem is in an initial position in contact with the proximal face of the valve seat forming a seal against distal fluid movement and the plurality of openings in the valve are unobstructed.

In some embodiments, when the valve is in the initial position, proximally directed force on the plunger causes the stopper causes the distal end of the valve stem to move proximally from the proximal face of the valve seat allowing fluid to flow from a blood vessel towards the cap, and then into the chamber. In one or more embodiments, subsequent distally directed force on the plunger causes the distal end of the valve stem to pass from a proximal side of the valve seat to a distal side of the valve seat moving the valve to the open position allowing fluid communication between the cap and the chamber through the plurality of openings in the valve.

In some embodiments, when distally directed force is applied to the stopper, the valve stem is not in complete contact with the valve seat and when a proximally directed force or no-force is applied to the stopper, the proximal side of valve stem is in complete contact with the distal end of valve seat to form a fluid-tight seal isolating the chamber from the IV line.

In some embodiments, the flush syringe assembly further comprises a sleeve and a disinfecting system. The sleeve is coaxial with the barrel and having a distal end and a proximal end, and an inside surface and an outside surface, wherein the sleeve slides from a distal position to a proximal position relative to the barrel. The disinfecting system comprising a disinfectant contained in a hub wherein the disinfectant system is released upon proximal motion of the sleeve.

In some embodiments, the sleeve further comprises one or more cutouts to provide visibility to the contents of the barrel. In one or more embodiments, the outside surface of the barrel further comprises two annular positioning ridges, a distal annular positioning ridge and a proximal annular positioning ridge. In some embodiments, the inside surface of the sleeve further comprises two annular positioning grooves for controlling the position of the sleeve relative to the barrel by engaging with the annular positioning ridges on the outside surface of the barrel.

In some embodiments, the distal end of the sleeve connected to the disinfectant system by an interference fit.

In one or more embodiments, the disinfecting system further comprises a removable cover for protecting the disinfectant system prior to use and a disinfectant-carrying medium.

In some embodiments, the stopper is made of material selected from the list consisting of thermoplastic elastomers, natural rubber, synthetic rubber, thermoplastic materials and combinations thereof.

In one or more embodiments, the cap engages with the VAD by one or more of threads that engage with complementary threads on the VAD or an interference fit.

BRIEF DESCRIPTION OF THE DRAWINGS

So that the manner in which the above recited features of the invention are attained and can be understood in detail, a more particular description of the invention, briefly summarized above, may be had by reference to the embodiments thereof which are illustrated in the appended drawings. It is to be noted, however, that the appended drawings illustrate only typical embodiments of this invention and are therefore not to be considered limiting of its scope, for the invention may admit to other equally effective embodiments.

FIG. 5 shows a schematic view of a syringe assembly according to one or more embodiments of the invention;

FIG. 6 shows a cross-sectional view of the syringe assembly of FIG. 5;

FIG. 12 shows a side view of a syringe assembly with a vascular access device attached in accordance with one or more embodiments of the invention;

FIG. 13 shows a cross-sectional view of the syringe assembly of FIG. 12 with the plunger in a proximal position;

FIG. 16 shows a side view of a syringe assembly with a vascular access device connected and the plunger rod in the distal position in accordance with one or more embodiments of the invention;

FIG. 17 shows a cross-sectional view of the syringe assembly of FIG. 16;

FIG. 27 shows a side view of a syringe assembly with the plunger rod in the proximal position in accordance with one or more embodiments of the invention;

FIG. 28 shows a cross-sectional view of the syringe assembly of FIG. 27;

DETAILED DESCRIPTION

Figure 1:
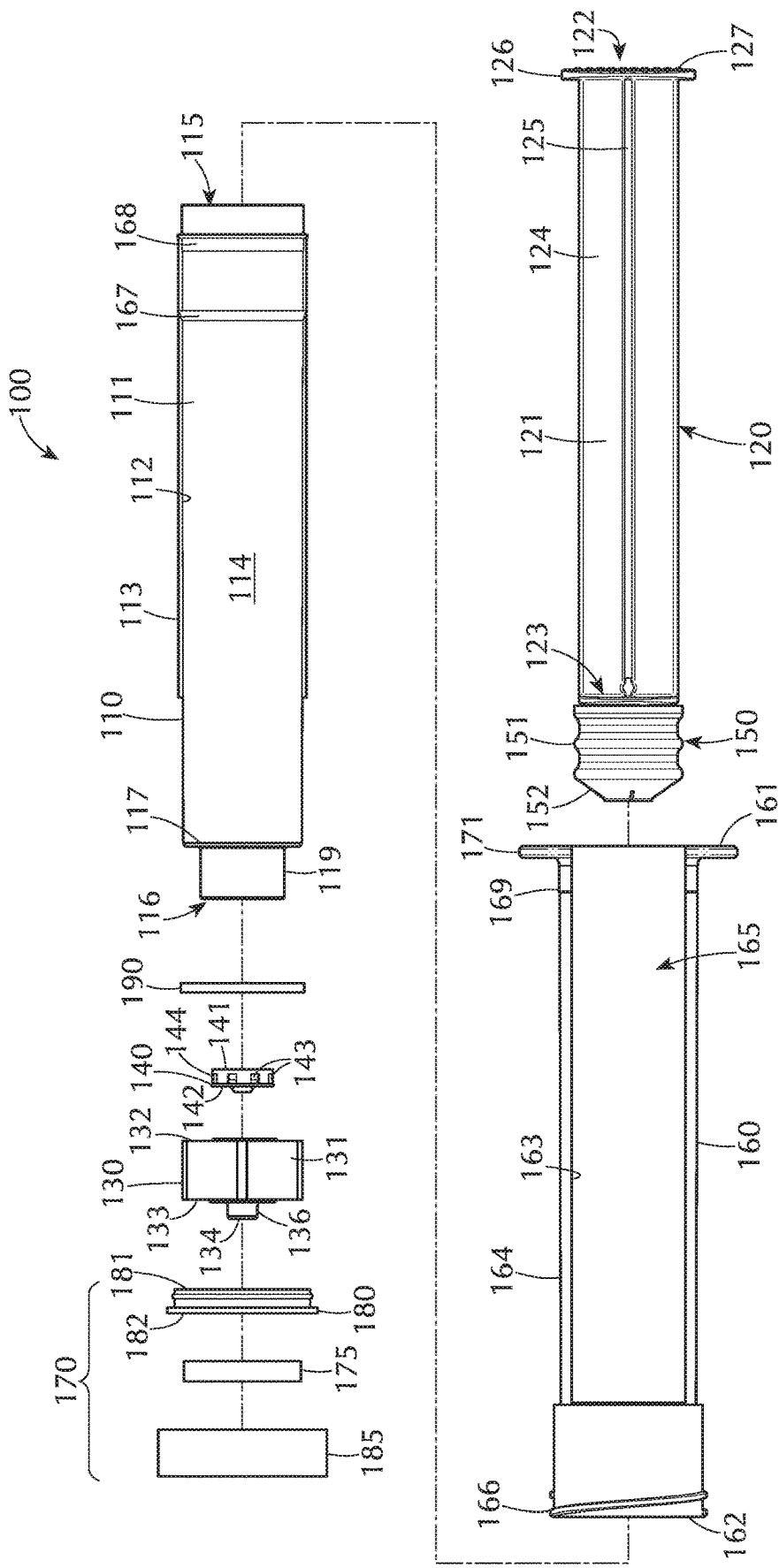
FIG. 1 shows an exploded schematic view of a syringe assembly according to one or more embodiments of the invention.

Embodiments of the invention are directed to syringe assemblies with valves and plugs which allow for one or more of prevention of blood reflux, elimination of the need for catheter positive displacement connectors and protection of the IV connector by capping of the IV connector.

The devices may prevent blood reflux into IV catheter lumens, after the catheter flushing procedure, eliminate the need for IV catheter positive displacement connectors or valves and/or protect the IV connector from contamination by capping the IV connector. These systems have the potential to extend catheter dwell times, reduce the use of Cathflo® (t-PA, Alteplase), and cap IV connectors to reduce the risk for connector inlet port bacterial colonization. One or more embodiments are directed to systems for disinfecting/cleaning connectors, flushing IV lines, preventing reflux, capping/sealing connector inlet port surfaces (e.g., to prevent microorganisms from entering IV lines or populate the connector inlet port surfaces).

In a first aspect, the user connects a luer cap to a catheter (or vascular access device) connector and flushes the line. The clinician flushing the VAD line pushes on the plunger rod of the flush syringe assembly moving the stopper toward the valve (or plug) displacing the fluid inside the syringe (which may be pre-filled or filled by the user). As the clinician completes the flushing process, they will push the plug into the distal end of the luer cap. The plug will be pushed into the luer cap by the stopper/plunger. This step will seal the lumen of the luer cap and prevent reflux. Since the plug displaces fluid in the direction of the IV line (or VAD), blood reflux into the catheter (or VAD) is prevented. After the luer cap's lumen is sealed with the plug, the user unscrews the barrel, stopper and plunger rod assembly from the luer cap and plug assembly. At this point, the luer cap and plug assembly have capped the catheter (or VAD) connector. The barrel, stopper and plunger rod assembly can be discarded.

In a second aspect, the fluid is only allowed to flow in the direction of the IV line (or VAD). When there is no flow, a one-way valve will be in the closed position. After the clinician connects the flush syringe to the IV (or VAD) connector, they will press on the plunger rod, which will cause the one-way valve to open and allow fluid to flow. When the clinician presses on the plunger rod, the pressure in the system unseats the valve stem and fluid will flow through the flow channels and enter the IV line (or VAD). When the clinician stops pressing on the plunger rod, the stopper will lock in position, and it will not allow liquid to flow back into the barrel. Simultaneously, the valve will close displacing the liquid in the IV (or VAD) line direction and preventing blood reflux. When the stopper stops moving, the valve will go from the open position to the closed position. The stopper can lock into position to prevent back flow into the barrel. The elastomeric flow channel in the valve and/or "spring" pulls back the valve stem and closes the valve. When the flushing procedure is completed, the user unscrews the barrel, stopper and plunger rod assembly form the luer cap/one-way valve assembly. The catheter (or VAD) connector will be capped and sealed by the luer cap/one-way valve assembly.

A third aspect is a combination of the first aspect and second aspect. The elastomeric "spring" flow channel will also function as a plug. Fluid will only be allowed to flow in the direction of the IV (or VAD) line. When there is no flow, the one-way valve will be in the closed position. After clinicians connect the flush syringe to the IV (or VAD) connector, they will press on the plunger rod, which will cause the one-way valve to open and allow fluid to flow. When clinicians press on the plunger rod, the pressure in the system will unseat the valve stem and fluid will flow through the flow channels of the valve and enter the IV (or VAD) line. When clinicians stop pressing on the plunger rod, the stopper will lock in position, and it will not allow liquid to flow back in to the barrel. Simultaneously, the valve will close displacing the liquid in the IV (or VAD) line direction and prevent blood reflux. The elastomeric flow channel and/or "spring" pulls back the valve stem and closes the valve. As clinicians complete the flushing process, they will push the elastomeric flow-channel/plug into the distal end of the one-way valve/luer cap and the plug will be pushed into the seal position by the stopper/plunger rod. This step will seal the lumen of the one-way valve/luer cap and prevent reflux. Since the plug displaces fluid in the direction of the IV (or VAD) line, blood reflux into the catheter (or VAD) is prevented. The clinician presses on the thumb press of the plunger rod to insert the plug into the luer cap. When the flushing procedure is completed, the user unscrews the barrel, stopper and plunger rod assembly form the luer cap/one-way valve assembly. The catheter (or VAD) connector will be capped and sealed by the luer cap/one-way valve assembly.

A fourth aspect is directed to a two-way valve system that converts to a one-way valve. Aspects of this sort address the need for drawing blood to check for catheter patency. Initially, the valve system will be a two-way valve to allow for blood withdrawal. However, once flushing starts the valve will turn to a one-way valve system to prevent blood reflux. This can also be designed as an independent device, and 'add-on' or accessory to the current flush syringe, or any other IV therapy device. The initial position of the valve stem is behind the valve seat. When clinicians pull the plunger rod to check for patency, the pressure of the system will unseat the valve stem from the back of the valve seat and fluid flow will be towards the flush syringe (i.e., into the syringe barrel). When clinicians stop pulling on the plunger rod, the valve stem will move back to its initial position (i.e., behind the valve seat). Stated differently, when the stock room plunger rod or in static condition the valve stem will move back to its default position. When clinicians push on the plunger rod to flush the IV catheter, the pressure in the syringe will force the valve stem to move across the valve seat and flow will be in the direction of the IV catheter. When clinicians stop pressing on the plunger rod, the stopper will lock in position and will not allow liquid to flow back into the barrel. Simultaneously, the valve will close displacing the liquid in the IV line direction and that will prevent blood reflux. The interference between the valve stem and the valve seat will not allow the valve stem to move back to its original or default position (i.e., behind the valve seat). Therefore, the valve stem will seat on the valve seat closing the valve (i.e., the valve will be in the closed position). When the flushing procedure is completed, the user unscrews the barrel, stopper and plunger rod assembly form the luer cap/one-way valve assembly. The catheter (or VAD) connector will be capped and sealed by the luer cap/one-way valve assembly.

In one or more embodiments, a valve operates as a plug system to prevent blood reflux into the IV catheter. As used in this specification and the appended claims, the term "valve" is used to describe a component which can allow fluid flow or block fluid flow depending on, for example, the direction of flow of the fluid and the position of the valve. The syringe assembly utilizes a plug that plugs the distal end of the Luer cap. The plug will be located at the distal end of the Luer cap, and it has flow channels that may allow for fluid transportation from the flush syringe to the catheter. In some embodiments, a one-way valve system is employed to prevent blood reflux into an IV catheter. The one-way valve allows flow substantially in the direction of the IV catheter only. In some embodiments, a two-way valve system converts to a one-way valve. Embodiments of this sort have a valve mechanism that is a two-way valve at the initial step of the flushing procedure. The two-way valve may allow for blood withdrawal (i.e., to check for IV line patency), when flushing starts, the two-way valve turns into a one-way valve (i.e., to prevent blood reflux).

FIGS. 1-19 show an embodiment of the invention incorporating a plug-like valve. Those skilled in the art will understand that the syringe assembly shown is merely one embodiment and that the syringe assembly can have different structures and components. Accordingly, one or more embodiments of the invention are directed to flush syringe assemblies 100 including a barrel 110, an elongate plunger rod 120, a cap 130 and a valve 140.

The barrel 110 has a side wall 111 with an inside surface 112 defining a chamber 114 for retaining a fluid, an outside surface 113, an open proximal end 115 and a distal end 116. The distal end 116 includes a distal wall 117 with an aperture 118 therethrough (shown in FIG. 7) in fluid communication with the chamber 114 allowing a fluid within the chamber 114 to exit the chamber through the aperture 118.

The outside surface 113 of the barrel 110 can be smooth or textured depending on the desired frictional quality of the resulting syringe assembly 100. For example, a textured outside surface 113 may offer the user a more stable and secure grip than a smooth surface. Additionally, the roughness or frictional feel of the outside surface 113 may be modified by the chemical composition of the material used in the syringe barrel 110.

The barrel 110 may also include a tip 119 which extends distally from the barrel 110. The tip 119 can have an outer diameter that is different from or the same as the outer diameter of the rest of the barrel 110. For example, as shown in the Figures, the outer diameter of the tip 119 has a smaller outer diameter than the barrel portion that is proximal of the tip 119. The tip 119 of the barrel 110 may include a luer slip connection (not shown) or a locking luer type collar concentrically surrounding the tip 119. The tip 119 shown in the Figures is a luer lock type connector and can be seen, for example, in FIG. 7.

Figure 2:
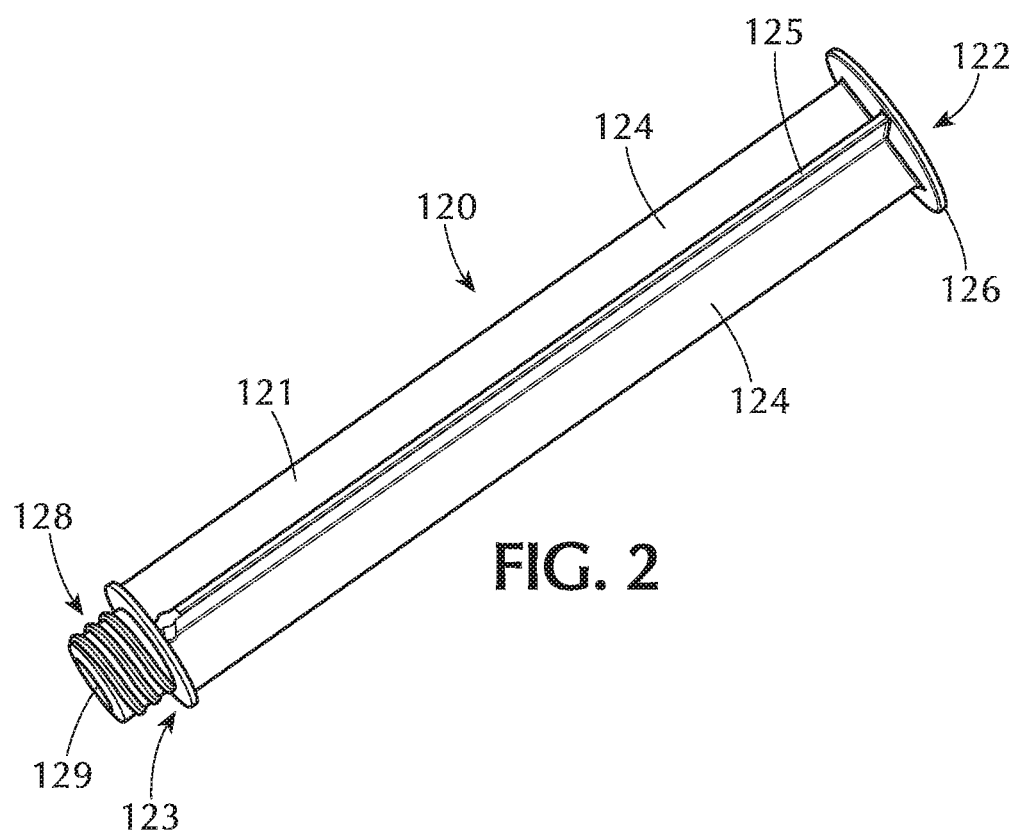
FIG. 2 shows a plunger rod in accordance with one or more embodiments of the invention.

An elongate plunger rod 120 is disposed within the barrel 110. FIG. 2 shows an isometric view of a plunger rod 120 in accordance with one or more embodiments. The plunger rod 120 includes an elongate body portion 121 with a proximal end 122 and a distal end 123. The plunger rod 120 shown in FIG. 1 includes a stopper 150 located on the distal end 123 of the plunger rod 120. The shape and size of the stopper 150 can be any suitable shape or size depending on, for example, the shape and size of the barrel 110 and plunger rod 120. The plunger rod 120 is slidably positioned in the barrel 110 so that the stopper 150 is in fluid-tight contact with the inside surface 112 of the barrel 110 and so that distal movement of the plunger rod 120 relative to the barrel 110 causes the stopper 150 to push the fluid out of the barrel 110. The plunger rod 120 shown in FIG. 2 includes a connector 128 on the distal end 123 of the plunger rod 120. The connector 128 shown includes screw threads 129 to which a stopper 150, or other component, can be attached by cooperative interaction with screw threads on the stopper 150. It will be understood by those skilled in the art that there are other types of connectors 128 besides screw threads 129. For example, the connector may include one or more axially spaced rings about the outside surface of the connector 128. The spaced rings provide can cooperatively interact with one or more grooves in the stopper 150 to affix the stopper 150 to the distal end 123 of the plunger rod 120.

The stopper 150 can be connected to the distal end 123 of the elongate plunger rod 120 by any suitable means. In some embodiments, the stopper 150 is connected by a mechanical connection such as interaction of complementary screw threads and press-fit connections. The stopper 150 can be a single piece or multiple pieces. In some embodiments, the stopper 150 is multiple pieces having a stopper body 151 and a detachable stopper tip 152. In one or more embodiments, the stopper 150 includes a conically-shaped distal surface and the barrel 110 includes a conically-shaped inside surface at the distal wall 117. Those skilled in the art will understand that conically-shaped can also include frustoconical shapes. In some embodiments, the stopper 150 includes a shape that is complementary to the shape of the distal end of the barrel 110 so that the stopper 150 is effective to expel the contents of the chamber 114 through the distal end 116 of the barrel 110. The stopper 150 may be slidably positioned in fluid-tight engagement with the inside surface 112 of the barrel 110 for drawing fluid into and driving fluid out of the chamber 114. If the syringe assembly is prefilled from the manufacturer, the stopper 150 need not be used for or able to draw fluid into the barrel 110.

The stopper 150 may be made of any material suitable for providing a seal with the inside surface 112 of the barrel 110. For example, the stopper 150 may be made of thermoplastic elastomers, natural rubber, synthetic rubber or thermoplastic materials and combinations thereof. The stopper 150 may be integrally formed or composed of separate components of the same or different materials joined together. The plunger rod 120 may be made of material which is more rigid than the stopper 150 such as polypropylene, polyethylene and the like. Materials should be chosen to be compatible with the procedure being used.

The elongate body portion 121 of the plunger rod 120 has an axial length extending from the proximal end 122 to the distal end 123. The body portion 121 may include a single beam or features, which may have cylindrical or other shapes. As shown in the Figures, the body portion 121 is formed by two perpendicularly intersecting beams 124, 125. The beams may have a plus-shaped or cruciform cross-section. In the embodiment shown, the two intersecting beams 124, 125 intersect to form an outside surface outlining four quadrants that face the inside surface 112 of the barrel 110 and extend along the axial length from the proximal end 122 to the distal end 123 of the plunger rod 120. While the drawings show embodiments of the plunger rod with a cruciform cross-section, it will be understood by those skilled in the art that the shape and/or cross-section of the plunger rod can be any suitable shape or cross-section and that the embodiments of the invention are not limited to the shapes shown in the drawings.

The plunger rod 120 may also include a thumbpress 126 at the proximal end 122 of the elongate body portion 121. The shape of the thumbpress 126 can vary depending on the desired usage of the flush syringe assembly 100. The thumbpress 126 shown in the drawings is round, but it will be understood by those skilled in the art that this is merely representative of one possible shape. Other shapes include, but are not limited to, square, rectangular, triangular, oval, pentagonal, hexagonal and cruciform. The shape of the thumbpress 126 in some embodiments substantially matches the shape of the elongate body portion 121 of the plunger rod 120, the barrel 110 or other components.

In some embodiments, the thumbpress has a plurality of ridges 127 thereon. The ridges 127 may enhance the ability of the user to press the plunger rod 120 distally with respect to the barrel 110 by providing a surface with an increased coefficient of friction. The shape of the ridges 127 or the ridge pattern can be changed depending on the desired usage of the plunger rod 120. For example, the ridges 127 can be a series of parallel lines, or curved in a design. In one or more embodiments, the ridges 127 are shaped to form a logo. The ridges 127 can be integrally formed with the plunger rod 120 or can be separate pieces that are attached to the plunger rod. The surface of the ridges 127 can be textured differently from the plunger rod or can be the same. Ridges 127 with a textured surface may provide a greater increase in the coefficient of friction than smooth ridges.

Figure 20:
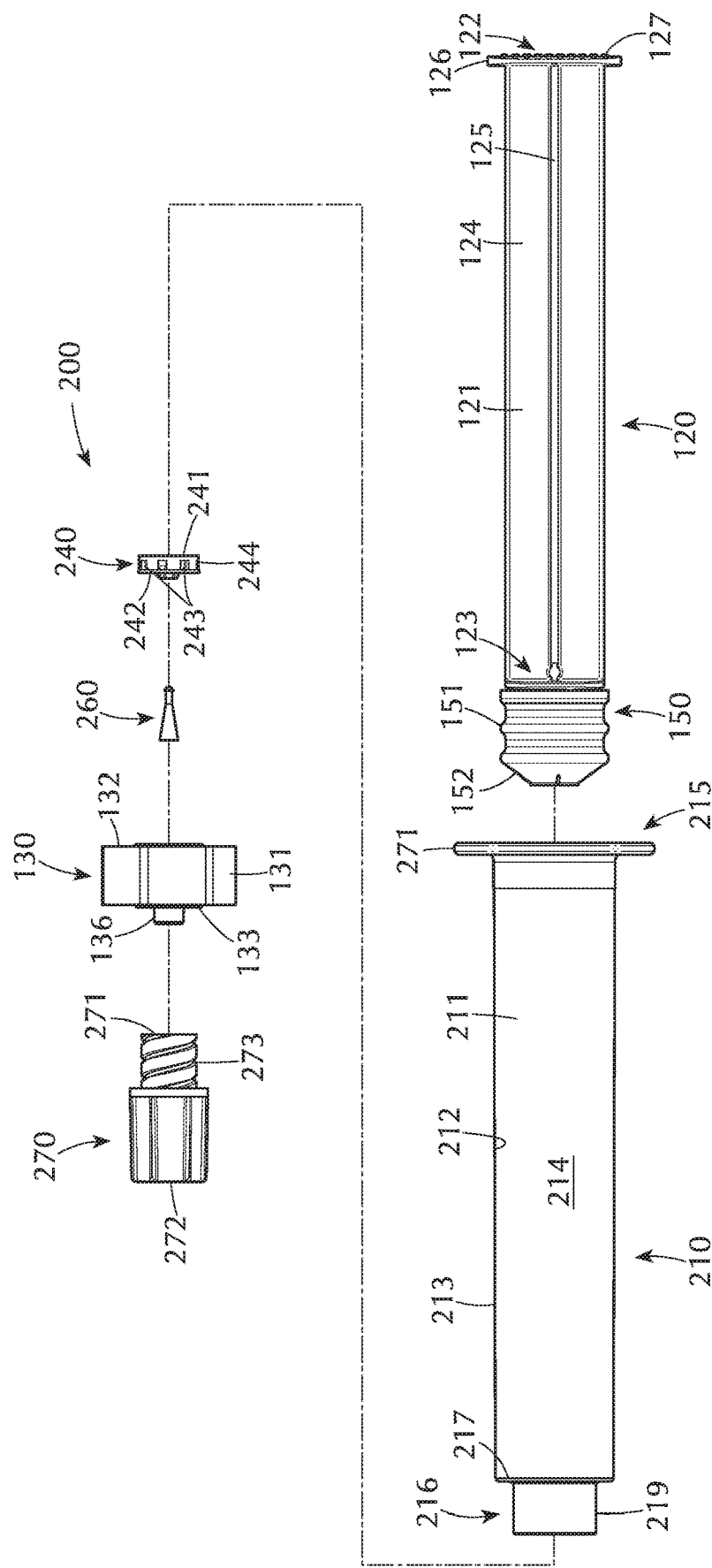
FIG. 20 shows an exploded side view of a syringe assembly in accordance with one or more embodiments of the invention.
Figure 21:
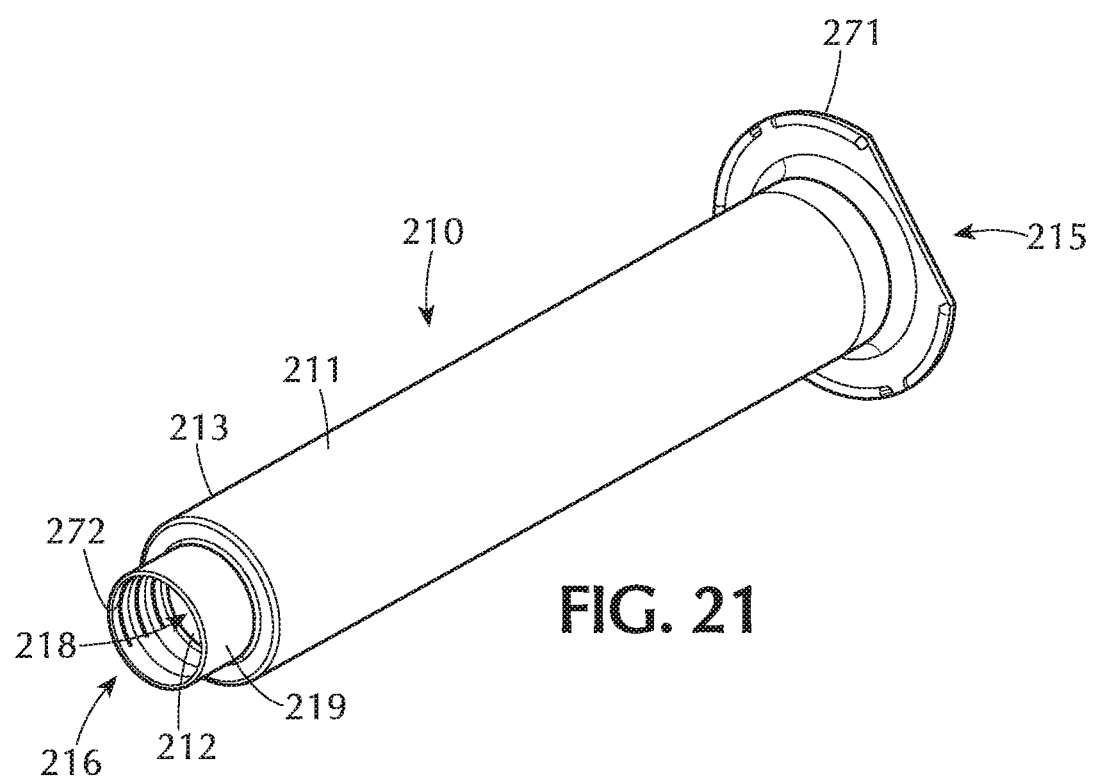
FIG. 21 shows a syringe barrel in accordance with one or more embodiments of the invention.

That cap 130 of various embodiments includes a body 131 with a proximal end 132, a distal end 133 and a tip 136 extending distally from the distal end 133. FIGS. 20 and 21 show a proximal view and distal view, respectively, of a cap 130 in accordance with one or more embodiment. Upon assembly, the proximal end 132 of the cap 130 is adjacent the distal end 116 of the barrel 110. The cap 130 comprises a passageway 134 extending through the tip and the body of the cap 130. The passageway allows for fluid communication between the chamber 114 of the barrel 110 and the device attached to the distal end 133 of the cap 130. This allows a fluid within the chamber 114 to be expelled through the distal end of the barrel 110 and through the cap 130 from the distal end 133 to the proximal end 132. The cross-sectional shape of the cap 130 can be any suitable shape including, but not limited to, triangular, square, pentagonal, hexagonal, heptagonal, octagonal, symmetric or non-symmetric polygonal. The shape of the cap 130 can provide a comfortable feel for the user and enhanced gripping ability to allow the user to easily connect or disconnect the cap from the barrel 110.

Figure 3:
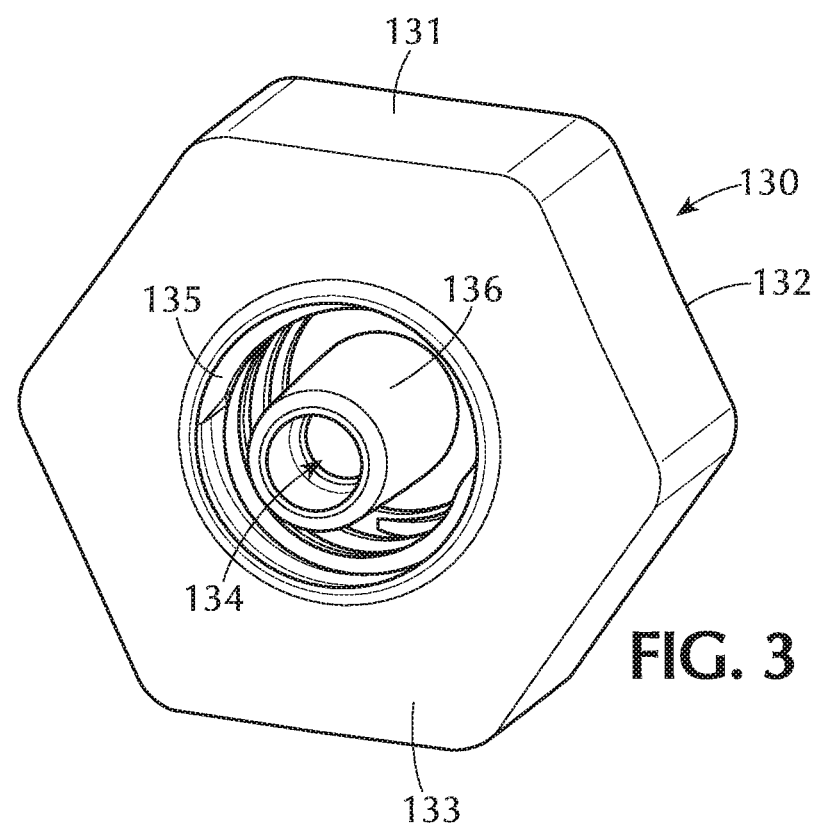
FIG. 3 shows a distal view of a cap in accordance with one or more embodiments of the invention.

The cap 130 includes a Luer connector 135 on the distal end 133, as shown in FIG. 3. The Luer connector 135 allows the cap 130, and any connected barrel 110, to be releasably connectable to a vascular access device (VAD). The Luer connector 135 shown in FIG. 3 is a Luer-Lok type connector comprising screw threads. However, the Luer connector can also be a Luer-slip type connector without screw threads.

Figure 4:
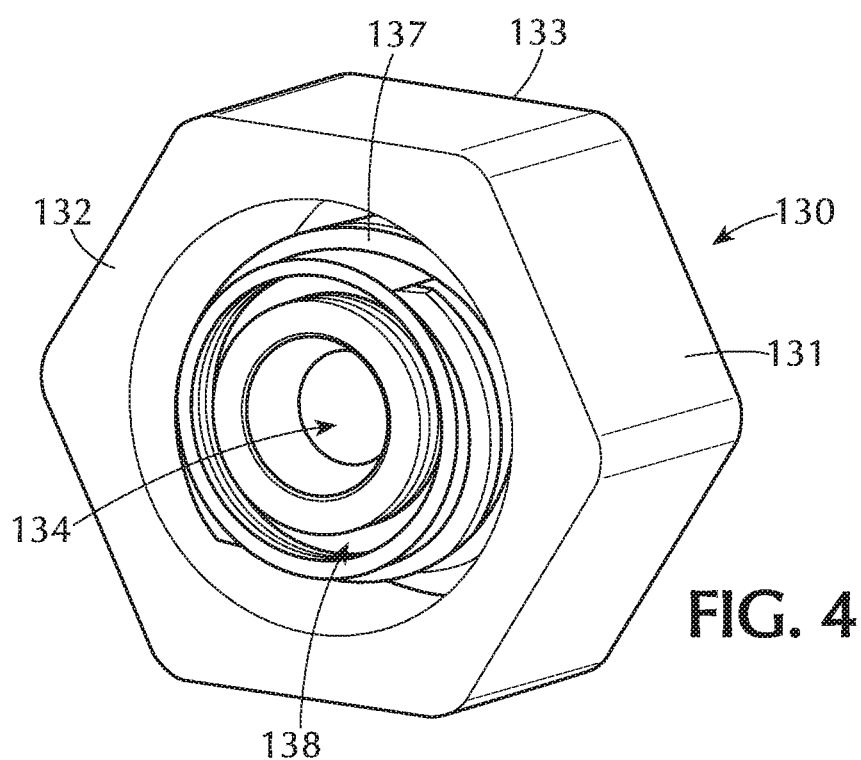
FIG. 4 shows a proximal view of a cap in accordance with one or more embodiments of the invention.

Additionally, the proximal end 132 of the cap 130 is releasably attachable to the barrel 110 via a suitable connector 137. Suitable connectors 137 include, but are not limited to, Luer slip and Luer-Lok type connectors. FIG. 4 shows the proximal end 132 of a cap 130 in accordance some embodiments. The connector 137 show in FIG. 4 is a Luer-Lok type connector.

A valve 140 is positioned adjacent the distal end 116 of the barrel 110 and the proximal end 132 of the cap 130. The valve 140 has a proximal face 141, a distal face 142 and a sidewall 144. In use, the valve 140 is positioned between the barrel 110 and the 130 so that the proximal face 141 of the valve 140 is positioned adjacent the distal end 116 of the barrel 110 and the distal face 142 is positioned adjacent the proximal end 132 of the 130. The valve 140 is movable between an open position and a closed position. In the open position, the valve 140 permits fluid to flow between the chamber 114 and the attached device. In the closed position, the valve 140 prevents fluid flow from the attached device, or blood vessel to the barrel when flushing of the IV line is completed.

In some embodiments, the flush syringe 100 includes a sleeve 160 and a disinfecting system 170. The sleeve 160 is coaxial with the barrel 110 and has a proximal end 161, a distal end 162, an inside surface 163 and an outside surface 164. The sleeve 160 can slide from a distal position to a proximal position relative to the barrel 110. The sleeve of some embodiments covers the cap 130 prior to use of the flush syringe assembly 100. The flush syringe assembly 100 can be packaged with the sleeve 160 already in place or as a separate component. The sleeve can be used to disengage the disinfectant carrier 175, described below, and/or cover the cap 130 until flushing of the vascular access device connection is complete.

The shape of the sleeve 160 can vary depending on the use of the device. For example, as shown in the drawings, the sleeve 160 is round, like the barrel 110, and sized to fit around the barrel 110. The sleeve 160 has one or more cutouts 165 which allow visibility of the barrel 110 and the contents therein. The sleeve can have any number of cutouts 165 including, but not limited to, one, two and three cutouts. For example, the sleeve 160 may have two cutouts 165 on opposite sides of the sleeve 160.

The distal end 162 of the sleeve 160, in some embodiments, has a threaded portion 166 which can be used to attach the disinfecting system 170. While a threaded portion 166 is shown, it will be understood by those skilled in the art that other attachment mechanisms can be used.

The disinfecting system 170 comprising a disinfectant carrier 175 and a hub 180. The hub 180 has a proximal face 181 and a distal face 182 and is sized to fit within the cover 185. The hub 180 can be made from any suitable material including, for example, a thermoplastic material. The distal face 182 of the hub 180 can be substantially flat or have a recessed section.

The disinfectant carrier 175 can be any suitable material capable of carrying and providing a disinfectant to the vascular access device. The disinfectant carrier 175 can be adhered to the distal face 182 of the hub 180 by any suitable means including, but not limited to, medical grade adhesive or tape. In one or more embodiments, the disinfectant carrier 175 is sized to fit within a recess in the distal face 182 of the hub 180 and can be secured there by either adhesive or a friction fit.

The disinfectant can be any suitable composition capable of cleaning the connection to the vascular access device. In one or more embodiments, the disinfectant carrier 175 is saturated with, or wetted with, a solution comprising the disinfectant. In some embodiments, the disinfectant comprises one or more disinfecting materials such as alcohol and antiseptic gels.

In some embodiments, the disinfecting system 170 further comprises a removable cover 185. The removable cover 185 is capable of protecting the disinfectant system prior to use including the disinfectant carrier 175. The removable cover 185 can be connected to either the hub 180 with the sleeve 160 by one or more of a friction fit or through engagement of complement retreads.

The disinfecting system 170 can be assembled on the distal end of the flush syringe assembly 100 in a number of configurations. In one or more embodiments, the disinfecting system 170 is arranged such that the disinfectant carrier 175 is fitted within a recess on the distal face 182 of the hub 180. The proximal face 181 of the hub 180 is positioned adjacent the distal face 133 of the cap 130 and is held in place by engagement with the inside surface of the distal end 162 of the sleeve 160 by either complementary screw threads or an interference fit. The cover 185 is positioned over the disinfectant carrier 175 and the hub 180 and is attached to the distal end 162 of the sleeve 160 by one or more of complement or the screw threads or interference fit. In one or more embodiments, the disinfecting system 170 is attached to the distal end 162 of the sleeve 160 by an interference fit (or a friction fit). In some embodiments, the disinfecting system 170 is attached to the distal end 162 of the sleeve 160 by engagement of complementary threads.

In one or more embodiments, the outside surface 113 of the barrel 110 includes a least one annular ridge 167. The annular ridge 167 is sized to provide a hindrance to spontaneous movement of the sleeve 160 relative to the barrel 110. The sentence can be provided by, for example, an interference fit or cooperative interaction between a complementary feature on the inside surface 163 of the sleeve 160. In some embodiments, the outside surface 113 of the barrel 110 includes at least two annular ridges 167, 168, as shown in FIGS. 1 through 8. Referring to FIG. 1, the annular positioning ridges comprise a distal annular positioning ridge 167 and a proximal annular positioning ridge 168. Also shown in FIG. 1, the sleeve 160 includes at least one annular positioning groove 169. The at least one annular positioning groove 169 is sized and positioned to help control the position of the sleeve 160 relative to the barrel 110 by engaging with the at least one annular positioning ridge 167, 168 on the outside surface 113 of the barrel 110.

In some embodiments, the sleeve 160 further comprises at least one handle 171 adjacent the proximal end 161 of the sleeve 160. The at least one handle 171 provides a region that can be gripped by the user to aide in the movement of the sleeve 160 relative to the barrel 110.

Some embodiments of the flush syringe assembly 100 further comprise a gasket 190. The gasket 190 can be sized to fit around the distal portion, including the tip 119, of the barrel 110 between the cap 130 and the distal wall 117 of the barrel 110. The gasket 190 can be made of any suitable material including, but not limited to, resilient rubber or plastic. The gasket 190 helps form a seal between the barrel 110 and the sleeve 160 and may have an outer diameter substantially equal to the outer diameter of the barrel 110 at the annular positioning ridges 167, 168. In some embodiments, there is an interference fit between the barrel 110 and the sleeve 160 without the need for a gasket 190.

FIGS. 5 and 6 show an embodiment of the flush syringe assembly 100 in initial state. The plunger rod 120 is positioned such that the stopper 150 is adjacent the proximal end 115 of the barrel 110. In this position, the chamber 114 has a maximum effective volume and can be either full of a medicament or empty. It will be understood by those skilled in the art that the flush syringe assembly 100 can be operated in the opposite fashion whereby in the initial state, the plunger rod 120 is positioned in the distal most position so that the cavity volume is minimized. Additionally, the plunger rod 120 can be initially positioned at any point between the proximal most position and the distal most position allowing for various uses and volumes of prefilled medicaments.

Figure 7:
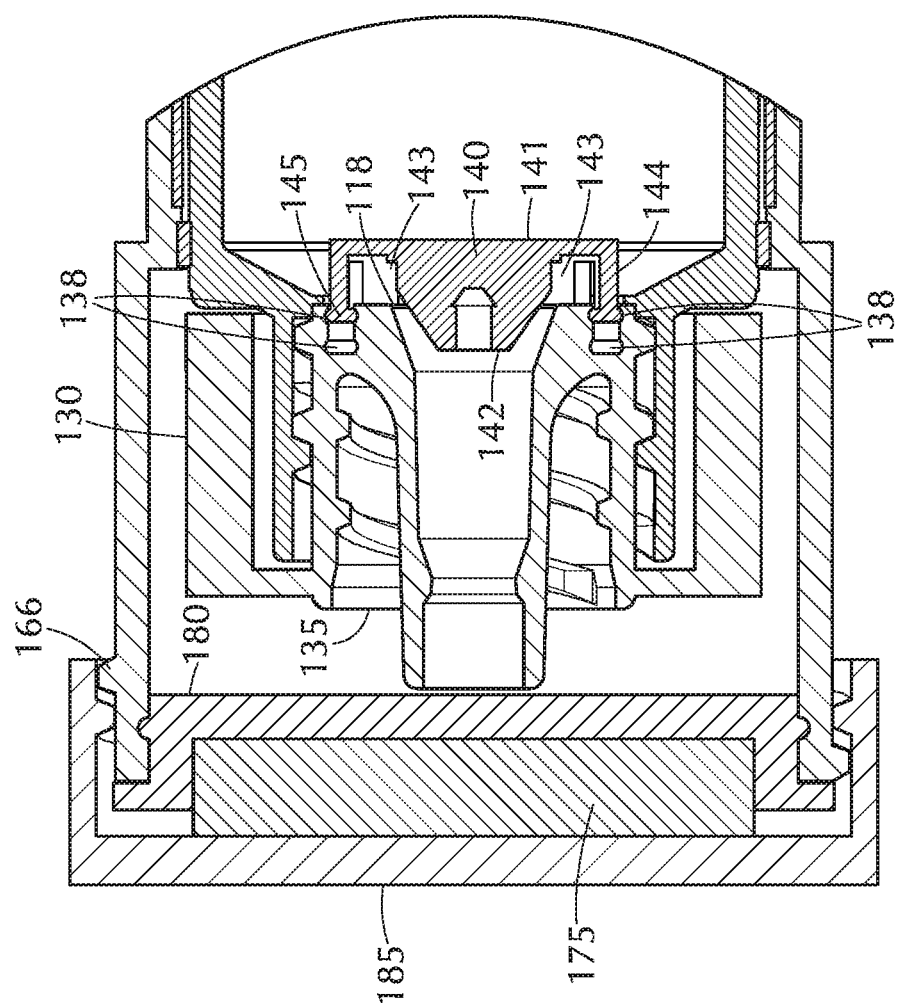
FIG. 7 shows an expanded cross-sectional view of the distal end of the syringe assembly of FIG. 6.

In the initial state, the disinfecting system 170 is connected to the distal end 162 of the sleeve 160 so that the hub 180 is connected to the sleeve with the disinfectant carrier 175 is positioned distally of the hub 180 and the cover 185 covers both the hub 180 and the disinfectant carrier 175. FIG. 7 shows an expanded view of the distal end of the flush syringe assembly 100 in the initial state with the disinfecting system 170. While other connections types can be used, the embodiment shown in the figures has the disinfecting system 170 connected to the sleeve 160 by cooperative interaction of screw threads on the outside of the sleeve 160 and the inside surface of the hub 180.

Figure 8:
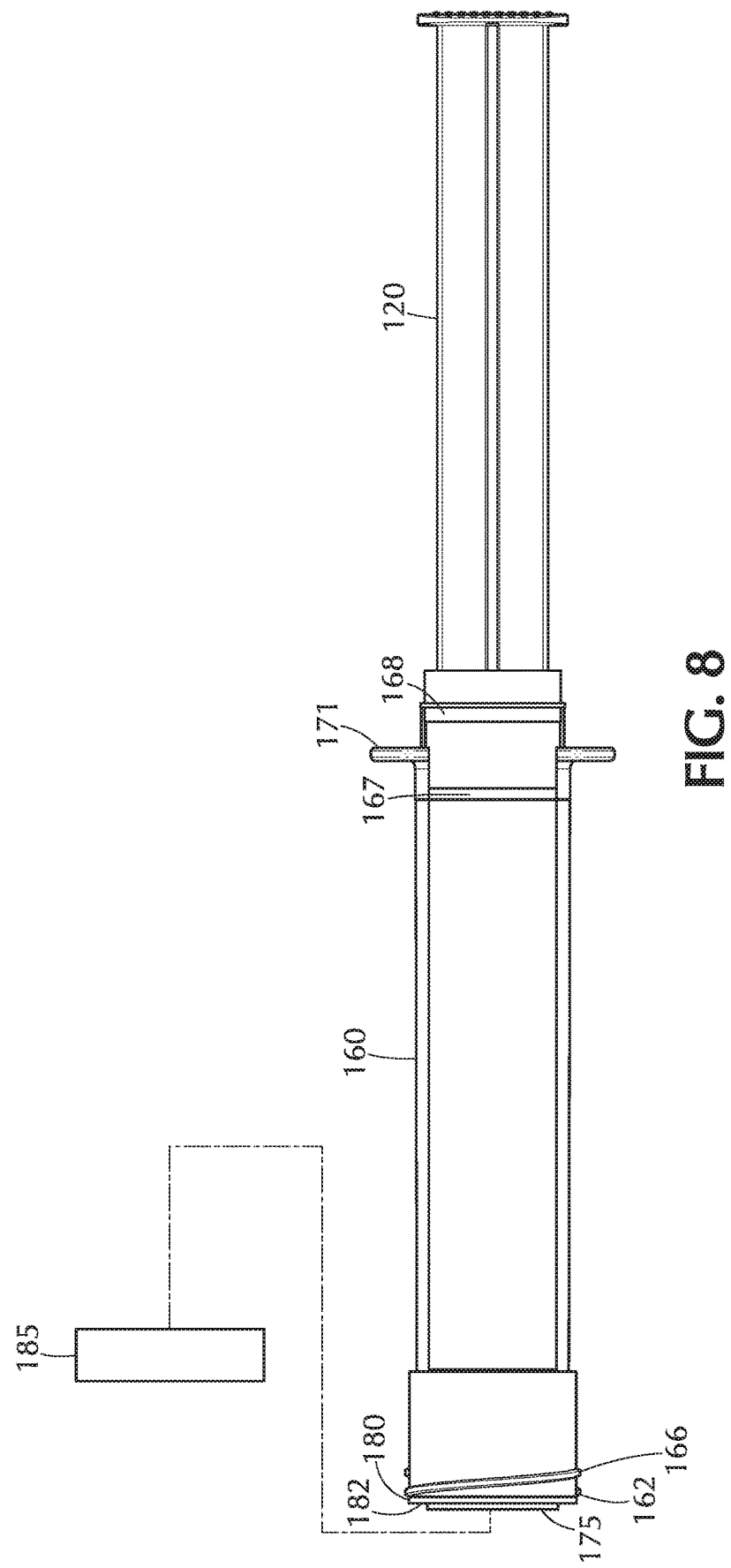
FIG. 8 shows a schematic view of a syringe assembly with the cap removed in accordance with one or more embodiments of the invention.
Figure 9:
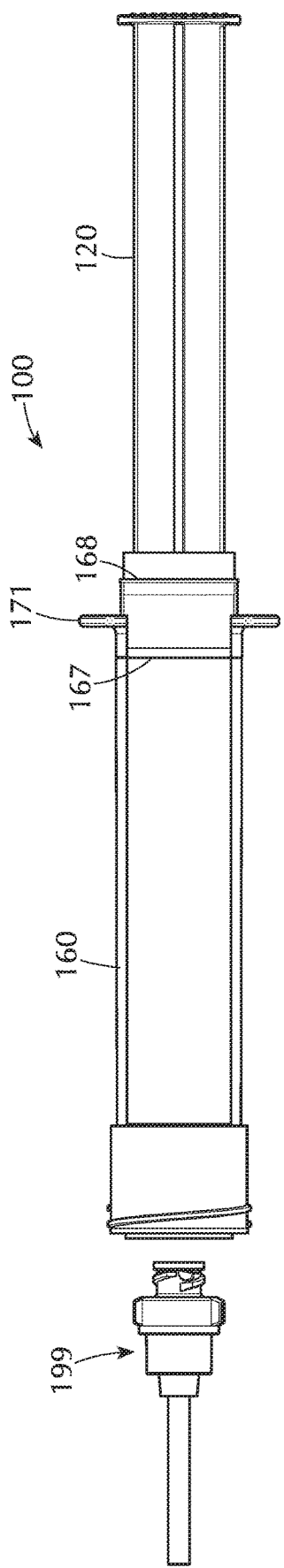
FIG. 9 shows a side view of a syringe assembly with the cap removed and an unconnected vascular access device in accordance with one or more embodiments of the invention.
Figure 10:
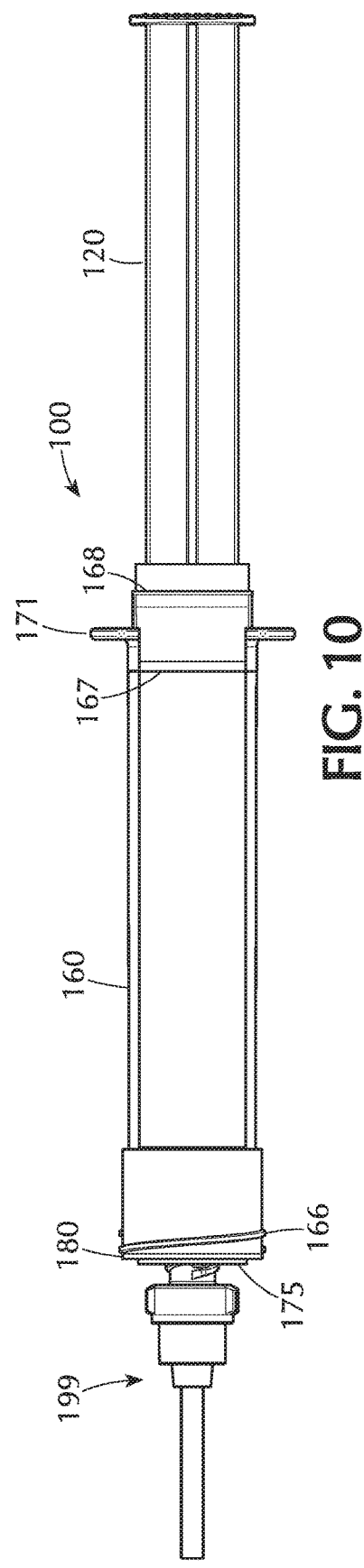
FIG. 10 shows a side view of the syringe assembly of FIG. 9 with the vascular access device connected in accordance with one or more embodiments of the invention.

As shown in FIG. 8, removal of the cover 185 exposes the disinfectant carrier 175 for use. The hub 180 and the distal face 182 of the hub 180 can be seen protruding slightly from the distal end 162 of the sleeve 160. With the disinfectant carrier 175 exposed, as shown in FIGS. 9 and 10, the user can clean the connection to the vascular access device 199 by contacting the disinfectant carrier 175 to the VAD 199.

Figure 11:
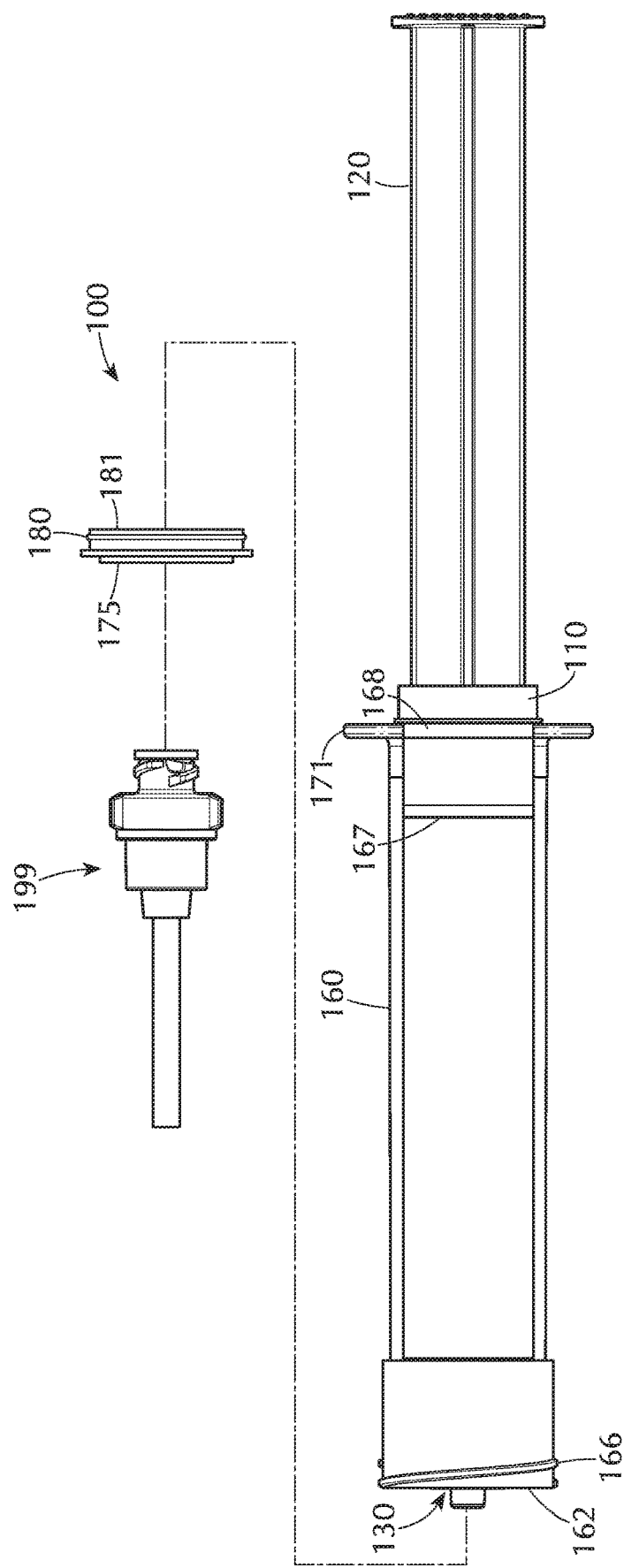
FIG. 11 shows an exploded side view of a syringe assembly with a vascular access device and hub removed in accordance with one or more embodiments of the invention.

After cleaning the vascular access device 199, the user applies proximally directed force on the sleeve 160 relative to the barrel 110. The proximally directed force can be applied to the sleeve 160 with the aide of the handle 171 on the sleeve 160. This proximally directed force causes the sleeve 160 to slide proximally relative to the barrel 110 so that the sleeve slides from the distal position where the distal positioning ridge 167 is located to the proximal position where the proximal positioning ridge 168 is located. Proximal movement of the sleeve 160 relative to the barrel 110 is equivalent to distal movement of the barrel 110 relative to the sleeve 160. This distal movement of the barrel 110 relative to the sleeve causes the tip of the cap 130 to press against the proximal face 181 of the hub 180, forcing the hub 180 to become disengaged from the distal end 162 of the sleeve 160. In the embodiment shown, the hub 180 is connected to distal end 162 of the sleeve 160 an interference fit so that distally directed pressure on the hub 180 can cause the hub 180 to pushed out of the sleeve 160 without requiring a twisting motion. FIG. 11 shows the flush syringe assembly 100 after cleaning the vascular access device 199 and disengagement of the hub 180. The distal end of the cap 130 can be seen extending from the distal end 162 of the sleeve 160.

After the disinfection system 170 has been removed from the distal end of the syringe assembly, the vascular access device 199, which is now clean, can be attached to the distal end 133 of the cap 130. FIGS. 12 and 13 show the flush syringe assembly after removal of the disinfection system 170 and attachment of the VAD 199 to the cap 130. The stopper 150 and plunger rod 120 are shown at a point midway along the length of the barrel 110. This is representative of a flush syringe assembly in which part of the medicament within the chamber 114 has been expelled through the cap 130 into the vascular access device 199.

Figure 14:
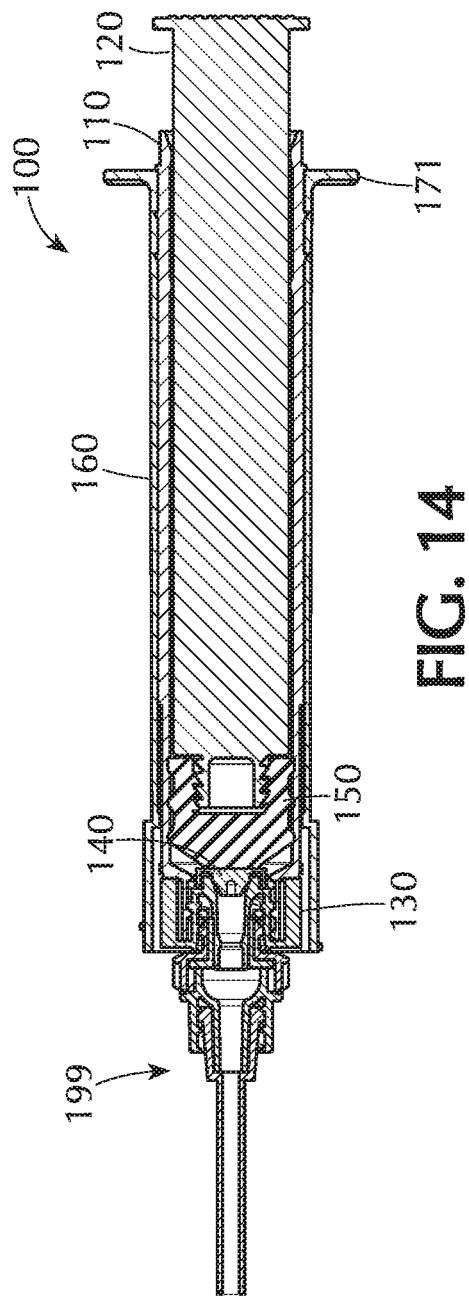
FIG. 14 shows a cross-sectional view of the syringe assembly of FIG. 12 with the plunger in the distal position.
Figure 15:
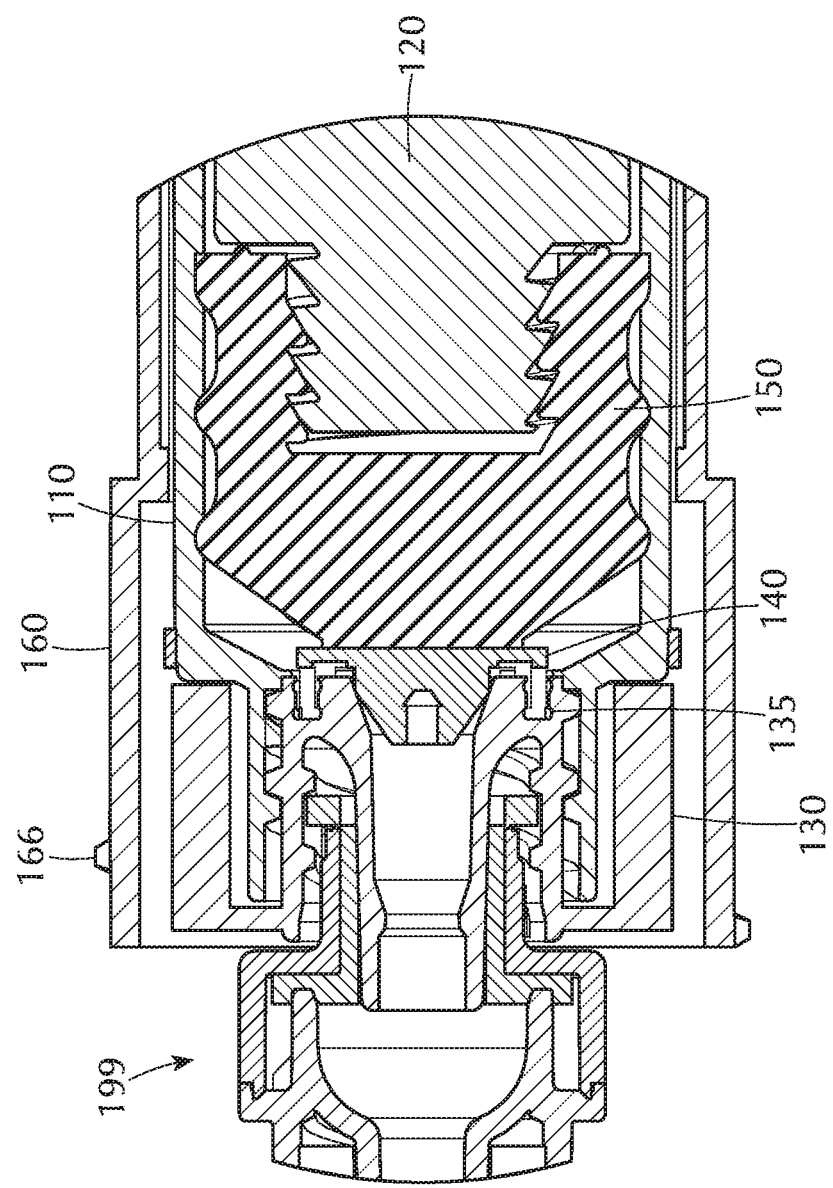
FIG. 15 shows an expanded cross-sectional view of the distal end of the syringe assembly of FIG. 14.
Figure 18:
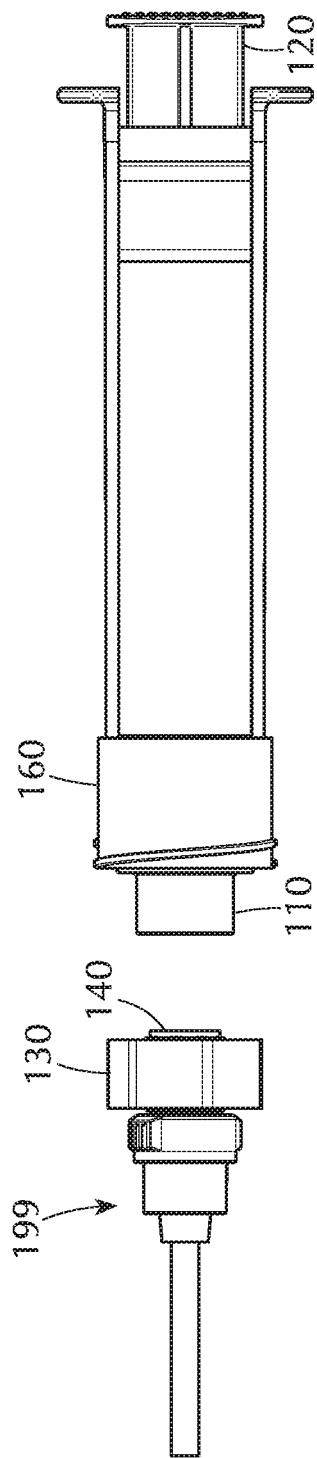
FIG. 18 shows a side view of a syringe assembly in with the vascular access device and cap removed in accordance with one or more embodiments of the invention.
Figure 19:
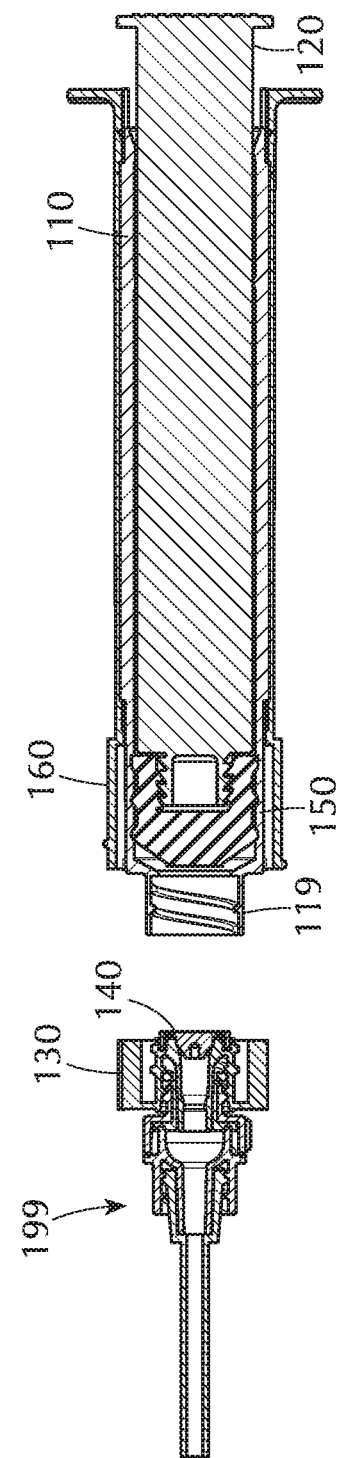
FIG. 19 shows a cross-sectional view of the syringe assembly of FIG. 18.

FIGS. 14 and 15 show the plunger rod 120 and stopper 150 in the distal most position. Here, the stopper 150 has applied a distally directed force to the valve 140, forcing the valve to move from the open position to the closed position.

Referring to the expanded views shown in FIGS. 7 and 15, it can be seen that the valve 140 can be moved from a proximal open position (FIG. 7) to a distal closed position (FIG. 12). In FIG. 7, there are a plurality of openings 143 in the valve 140 that are unobstructed, allowing fluid communication between the chamber 114 and the cap 130. In FIG. 15, after the valve 140 has been moved to the closed position, the plurality of openings 143 are obstructed preventing fluid communication between the chamber 114 and the cap 130.

In one or more embodiments, as shown in FIG. 7, the valve 140 comprises a plug having a proximal face 141 and a sidewall 144 extending distally therefrom. The sidewall 144 includes a plurality of openings 143 that allow fluid communication between the chamber 144 and the cap 130 (and any connected device such as an IV line). The plug 140 shown in the embodiment of FIGS. 1-19 has a plurality of openings 143 which, when unblocked, allow fluid communication between the chamber 114 of the barrel 110 and the cap 130. When blocked, the plurality of openings 143 substantially prevent fluid communication between the chamber 114 and the cap 130. As used in this specification and the appended claims, the term "substantially prevents" means that the fluid communication is nearly completely or completely blocked. While fluid flow is intended to be completely stopped, it will be understood by those skilled in the art that some small amount of unintended flow or potential flow may still remain.

Referring to FIG. 7, the valve 140, in this case a plug, is shown in the proximal position with the plurality of openings 143 allowing fluid communication between the chamber 114 and the cap 130. This may be the initial position of the valve 140. In use, the plunger rod 120 is moved distally so that the stopper 150 forces fluid within the chamber 114 out of the distal end of the barrel 110 through the plurality of openings 143 in the valve 140. The stopper 150 will contact the proximal face 141 of the valve 140 and further distal movement of the plunger rod 120 forces the valve 140 to move to the distal position. In the distal position, shown in FIG. 15, the valve 140 is pressed into the cap 130 and the plurality of openings 143 are blocked preventing additional fluid communication between the chamber 114 and the cap 130.

In some embodiments, as shown in FIGS. 7 and 15, the distal end 142 of the valve 140 includes lugs 145 which hinder spontaneous movement of the valve between the open and closed positions. The cap 130 in some embodiments can have one or more complementary recesses 138 to engage the lugs 145 and provide even greater hindrance to spontaneous movement of the valve 140. In the embodiment shown in FIG. 7, the cap 130 includes two recesses 138, one positioned to support the lugs 145 when the valve 140 is in the open position (FIG. 7) and one positioned distally to support the lugs 145 when the valve 140 is in the closed position (FIG. 15).

After the flush syringe is used, and the valve has been moved into the distal closed position, the cap 130 and valve 140 can be released from the distal end of the barrel 110 and left attached to the vascular access device. This is effective to cap off the vascular access device 199 to prevent contamination and minimize the need for future cleaning. Capping the VAD 199 also helps prevent blood refluxing through the VAD 199. FIGS. 13 and 14 show the flush syringe assembly 100 in which the chamber 114 has been emptied and the plunger rod 120 and stopper 150 have pressed the valve 140 into the closed position. Here, it can be seen that the sleeve 160 has been moved proximally relative to the barrel 110 so that the entire cap 130 is exposed from the distal end 162 of the sleeve 160. As shown in FIGS. 15 and 16, the cap 130 and valve 140 have been disengaged from the distal end of the barrel 110 and left connected to the vascular access device 199 to removably seal the VAD.

The valve 140, or plug, can be made from any suitable material. In some embodiments, the valve is made from a rigid material to minimize deflection of the valve during movement from the proximal open position to the distal closed position. In some embodiments, the valve is made of a flexible material. In one or more embodiments, the valve is a plug which is flexible. In some embodiments, the valve is made from a material comprising an elastomeric material.

FIG. 20 shows an exploded view of another embodiment of the invention comprising a one-way valve. For ease of description, similar components use similar reference numerals. For example, the plunger rod 120 shown in the embodiment of FIG. 20 is the same as the plunger rod 120 shown in the embodiment of FIG. 1.

The embodiment shown in FIG. 20 does not include the sleeve 160 and disinfecting system 170 of the embodiment of FIG. 1. Referring to FIGS. 20 and 21, the barrel 210 is similar to that of the FIG. 1 in that there is a side wall 211 with an inside surface 212 defining a chamber 214 for retaining a fluid, an outside surface 213, an open proximal end 215 and a distal end 216. The distal end 216 includes a distal wall 217 with an aperture 218 therethrough in fluid communication with the chamber 214 allowing a fluid within the chamber 214 to exit the chamber through the aperture 218.

Figure 26:
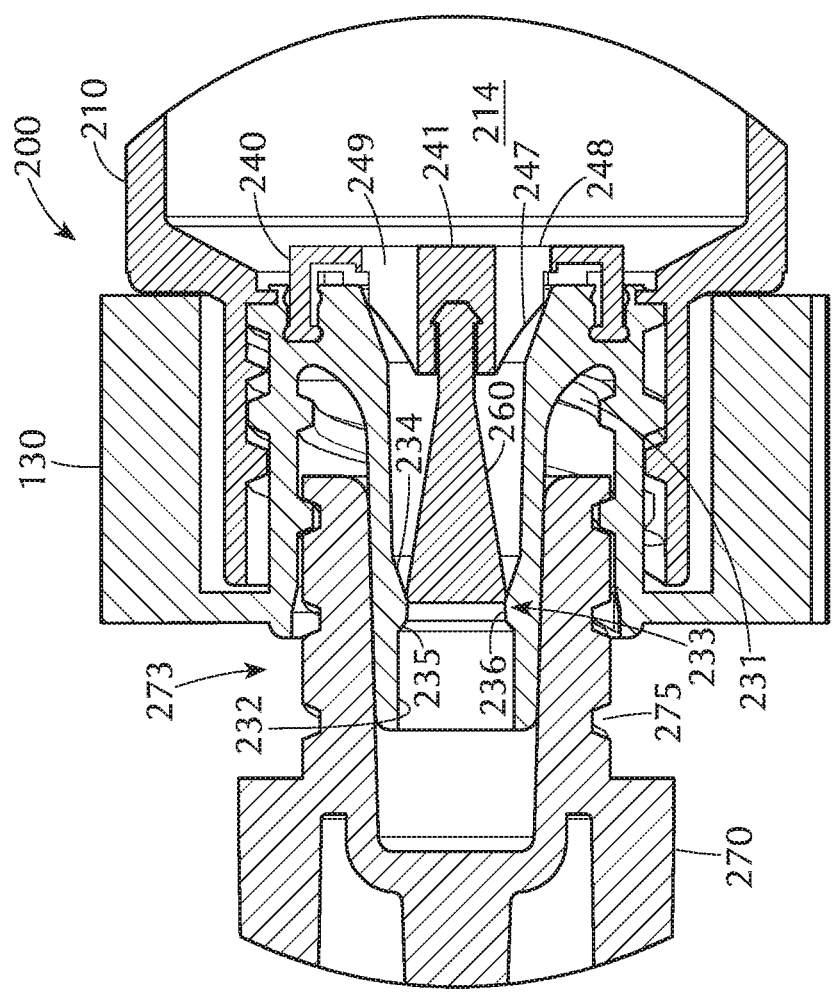
FIG. 26 shows an expanded cross-sectional view of a syringe assembly with a cap and vascular access device attached in accordance with one or more embodiments of the invention.

The barrel 210 may also include a tip 219 which extends distally from the barrel 210. The tip 219 can have an outer diameter that is different from or the same as the outer diameter of the rest of the barrel 210. For example, as shown in the FIGS. 20 and 21, the tip 219 has a smaller outer diameter than the barrel portion that is proximal of the tip 219. The tip 219 of the barrel 210 may include a luer slip connection (not shown) or a locking luer type collar concentrically surrounding the tip 219 or within the inside portion of the tip 219. The tip 219 shown in the Figures has a Luer-Lok type connection with screw threads 275 on the inside surface of the tip 219. As shown in FIG. 26, the screw threads 275 on the closure 270 cooperatively interact with screw threads on the proximal end 132 of the cap 130.

Since there is no sleeve 160 with handles 171 in the embodiment of FIG. 20, the barrel 210 includes a handle 271 adjacent the proximal end 215. The handle 271 can be a single handle extending partially or completely about the outside of the proximal end 215 of the barrel 210. In some embodiments, the handle 271 is multiple pieces, each extending partially about the outside surface of the barrel 210. As shown in FIG. 21, the shape of the handle 271 can change at different portions about the outside surface of the barrel 210.

Figure 22:
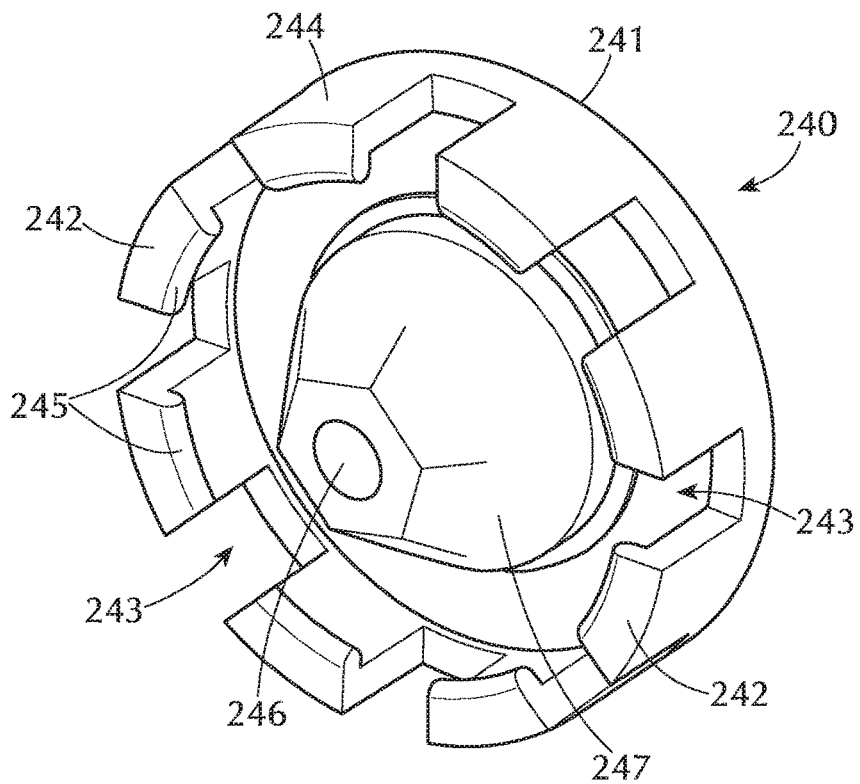
FIG. 22 shows a distal view of a valve in accordance with one or more embodiments of the invention.

FIG. 22 shows a valve 240 in accordance with one or more embodiments of the invention. This valve 240 can also be a plug, as that shown in the embodiment of FIG. 1. FIG. 22 is a perspective view of a distal end 242 of a valve 240. The valve 240 includes a proximal face 241 with a sidwall 244 extending distally therefrom. A plurality of openings 243 are radially spaced about the sidwall 244. The openings 243 shown open at the distal end 242 of the valve 240 interrupting the continuity of the distal end 242 of the valve 240. In some embodiments, the openings 243 are within the sidwall 244 so that the distal end 242 of the valve 240 is uninterrupted. The central portion of the distal end 242 of the valve has a frustoconically shaped projection 247. This projection 247 may provide mass, stability and rigidity to the valve 240 without interfering with the operation of the valve 240. The shape of the projection 247 can be any suitable shape and may be designed to cooperatively interact with a recess in the cap 130 to aid in the plugging of the vascular access device. The projection 247 shown in FIG. 22 has a circular base (closest to the proximal face 241) which transitions into a hexagonal top at the distal end. This is merely one possible shape for the projection 247 and should not be taken as limiting the scope of the invention.

The valve 240 includes an opening 246 in the center of the distal end of the projection 247. The opening 246 of some embodiments is sized to fit a proximal end of a valve stem 260 (described below). This opening 246 can be cylindrical with roughly straight sidewalls, or can be forward tapered (e.g., with the diameter of the distal end of the opening larger than the diameter of the proximal end) or reverse tapered (e.g., with the diameter of the proximal end of the opening larger than the diameter of the distal end of the opening). In some embodiments, the opening has a generally reverse tapered shape configured to cooperatively interact with a portion of the proximal end of the valve stem 260 to secure the valve stem in position.

Figure 23:
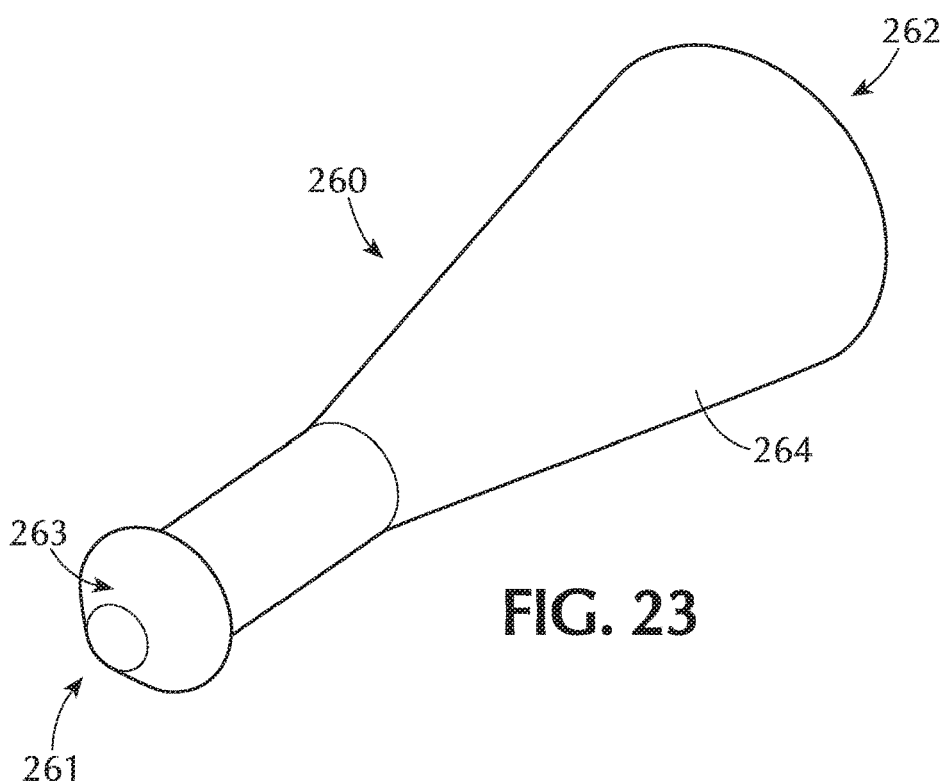
FIG. 23 shows a valve stem in accordance with one or more embodiments of the invention.

FIG. 23 shows a valve stem 260 in accordance with one or more embodiment of the invention. The valve stem 260 includes a proximal end 261 and a distal end 262. In some embodiments, the proximal end 261 of the valve stem includes a tapered portion 263 which is configured to cooperatively interact with an opening 246 in the distal end of a projection 247 on the valve 240. The distal end of the valve stem 260 includes a tapered portion 264 with the diameter of the tapered portion increasing toward the distal end 262 of the valve stem 260. The valve stem 260 has a proximal diameter and a distal diameter greater than the proximal diameter. The tapered portion 264 of some embodiments is sized and shaped to cooperatively interact with a valve seat on the inside surface of the cap 130 to form a fluid-tight seal when the valve stem 260 is in complete contact with the valve seat.

Figure 24:
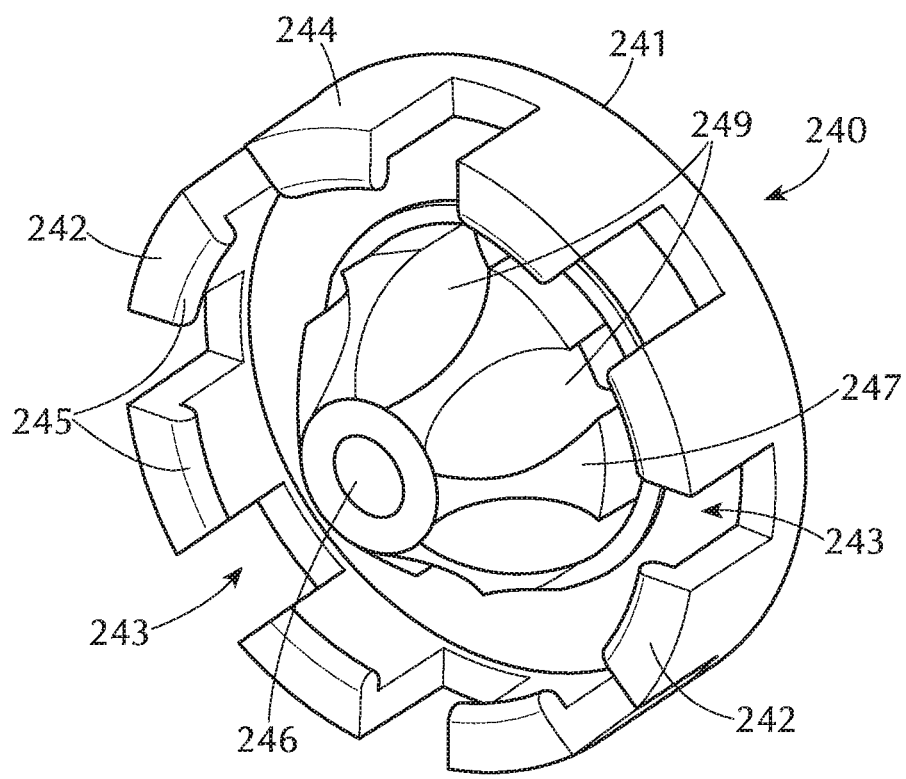
FIG. 24 shows a distal view of a valve in accordance with one or more embodiments of the invention.
Figure 25:
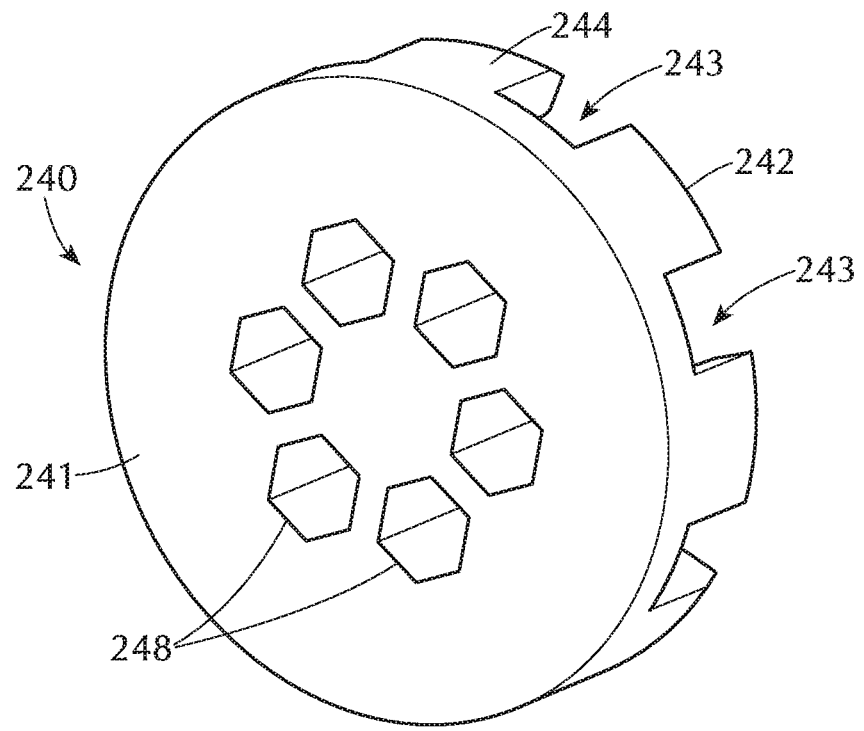
FIG. 25 shows a proximal view of a valve in accordance with one or more embodiments of the invention.

FIGS. 24 and 25 show an alternate embodiment of the a valve 240 in accordance with one or more embodiment of the invention. FIG. 24 shows a distal perspective view of the valve 240 and FIG. 25 shows a proximal perspective view of the valve 240. In the embodiment shown, the proximal face 241 comprises a plurality of openings 248 allowing fluid communication between the chamber 214 in the barrel 210 and the cap 130. Referring to FIG. 24, the openings 248 extend along the length of the projection 247 as a series of channels 249 so that the flow through the openings 248 is not hindered by the projection 247. The shape of the openings 248 and the channels 249 can independently be any suitable shape. For example, as shown in FIGS. 24 and 25, the openings 248 have a hexagonal shape at the proximal face 241 of the valve 240 and a circular shape along the length of the channels 249. It will be understood by those skilled in the art that the shape of the openings 248 and channels 249 shown are merely illustrative and should not be taken as limiting the scope of the invention.

Some embodiments of the invention further comprise a closure 270 having a proximal end 274 and a distal end 272. The proximal end 274 of the closure 270 has a connector 273 capable of cooperatively interacting with the distal end 133 of the cap 130. For example, if the cap 130 has a screw type connector, then the proximal end 274 of the closure 270 might have a mating screw type connector 273 with screw threads 275. If the cap 130 has a tapered connector for a Luer slip type connection, then the closure 270 might have a similarly tapered connector 273 instead of the screw threads 275 shown in the Figures. It will be understood by those skilled in the art that the screw threads 275 shown are merely illustrative and should not be taken as limiting the scope of the invention.

Referring to FIGS. 26 to 40, the operation of the flush syringe assembly 200 according to one or more embodiments is described. FIG. 26 shows an expanded view of the distal end of the flush syringe assembly 200 in the initial position and FIGS. 27 and 28 show a side view and cross-sectional side view, respectively, of the flush syringe assembly 200 in the initial position. The embodiments shown in FIGS. 26-40 includes a valve 240 and valve stem 260. The valve 240 shown is similar to the valve shown in FIGS. 24-25 in that there are a plurality of openings 248 in the proximal face 241 and a plurality of channels 249 in the projection 247 of the valve 240. It will be understood that the valve 240 shown can be substituted with the valve 240 shown in FIG. 22 which lacks the plurality of openings.

Referring again to FIG. 26, initially, the closure 270 is positioned at the distal end of the flush syringe assembly to seal the cap and prevent contamination of the device. The connector 273 of the closure 270 is shown with screw threads which mate with complementary screw threads 231 on the cap 130. It can be seen that the valve stem 260 is connected to the valve 240 with complementary tapered surfaces. This shape allows the proximal end of the valve stem 260 to be inserted into the opening 246 of the valve 240 but prevents the valve stem 260 from being easily removed from the valve 240. The distal end of the valve stem 260 rests against a proximal ramp 234 on the valve seat 233 located on the inner surface 232 of the cap 130. The valve seat 233 comprises a proximal ramp 234 and a distal ramp 235 forming a ring within the inner surface 232 of the cap 130. The valve seat 233 shown also includes an optional central portion 236 connecting the proximal ramp 234 and the distal ramp 235.

Figure 29:
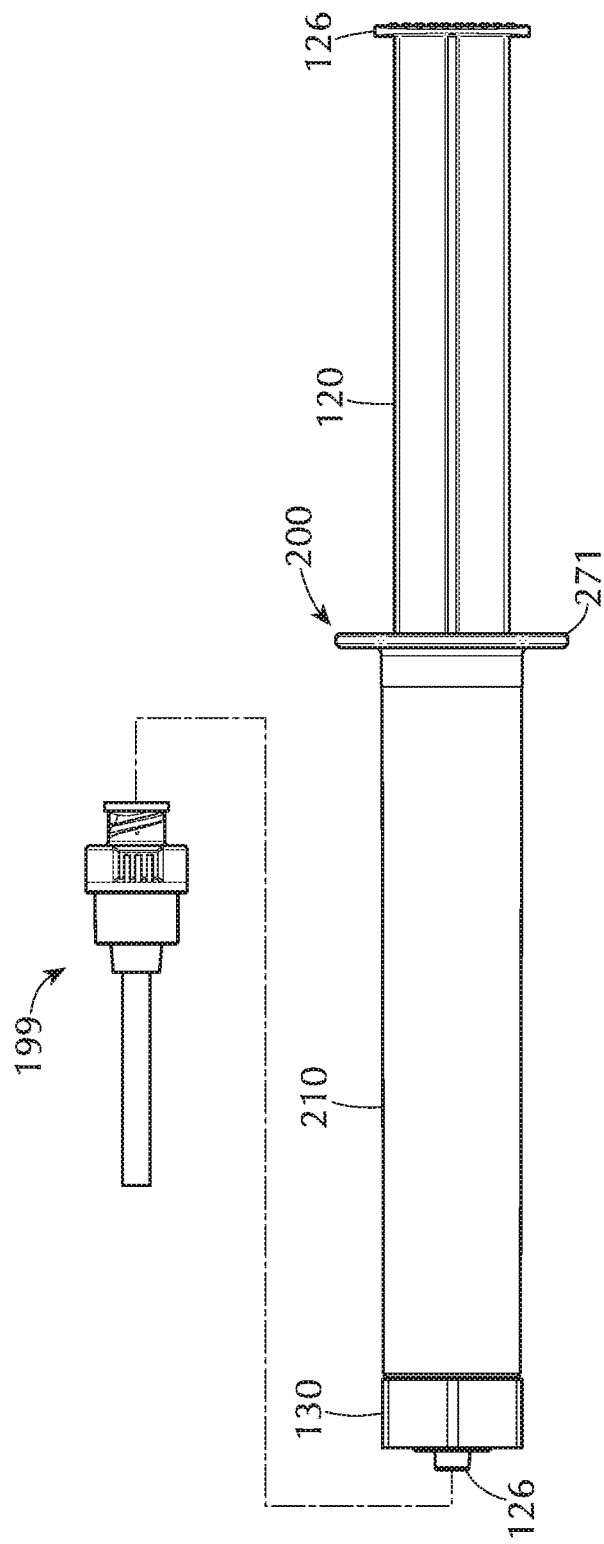
FIG. 29 shows an exploded side view of a syringe assembly with a vascular access device not attached in accordance with one or more embodiments of the invention.
Figure 30:
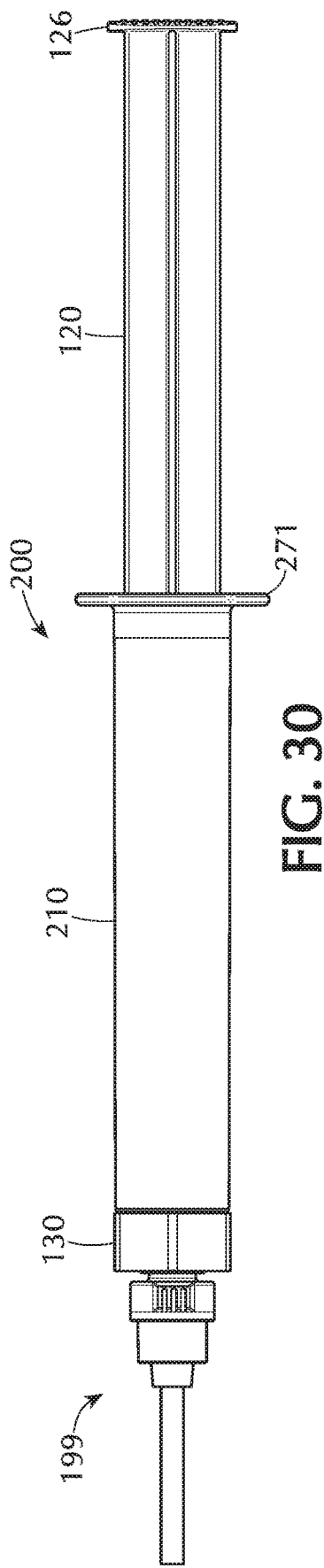
FIG. 30 shows a side view of the syringe assembly of FIG. 29 with the vascular access device attached in accordance with one or more embodiments of the invention.
Figure 31:
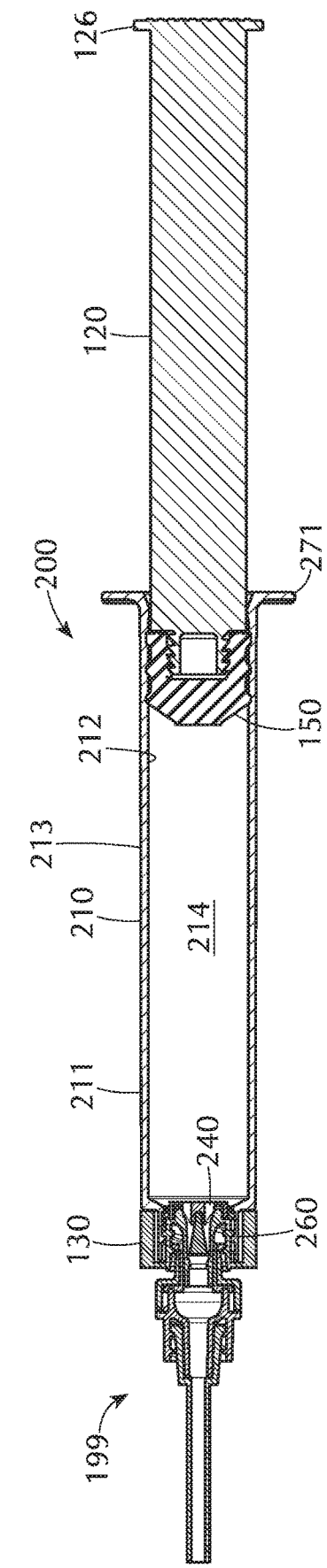
FIG. 31 shows a cross-sectional view of a syringe assembly with the plunger rod in the proximal position in accordance with one or more embodiments of the invention.

As shown in FIG. 29, the closure 270 is removed from the distal end of the flush syringe assembly 200 to expose the tip 136 of the cap 130. Referring to FIGS. 30 and 31, the vascular access device 199 can now be connected to the cap 130 by, in the embodiment shown, cooperative screw threads, or other connection types.

Figure 32:
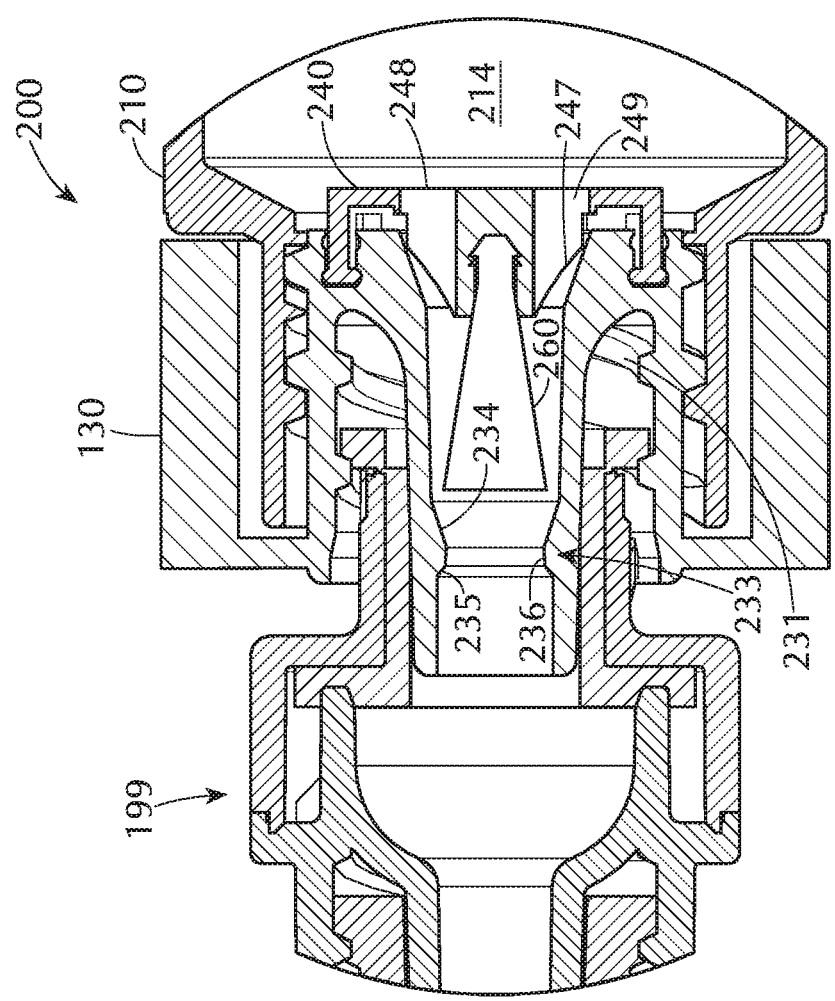
FIG. 32 shows an expanded cross-sectional view of the distal end of the syringe assembly of FIG. 31.

As shown in FIG. 32, drawing the plunger rod in the proximal direction causes the valve stem 260 to flex or compress in the proximal direction. This creates a gap between the valve stem 260 and the valve seat 233 which allows fluid to flow from the vascular access device 199 through the cap 130 toward the chamber 214. If the valve has no holes in the proximal face 241, then the fluid flows through the plurality of openings in the sidewall 244. If there are holes in the proximal face 241, the fluid can flow through either or both of the holes in the proximal face 241 and the openings in the sidewall 244. If there are no openings in the sidewall 244, then the fluid can flow through the holes in the proximal face 241.

Figure 33:
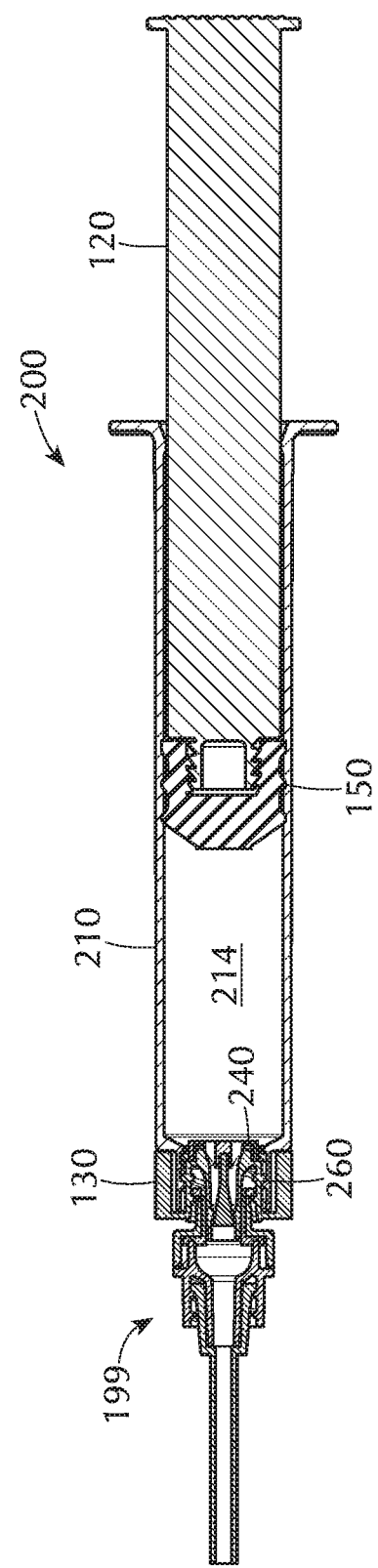
FIG. 33 show a cross-sectional side view of a syringe assembly with the plunger rod in the proximal position in accordance with one or more embodiments of the invention.
Figure 34:
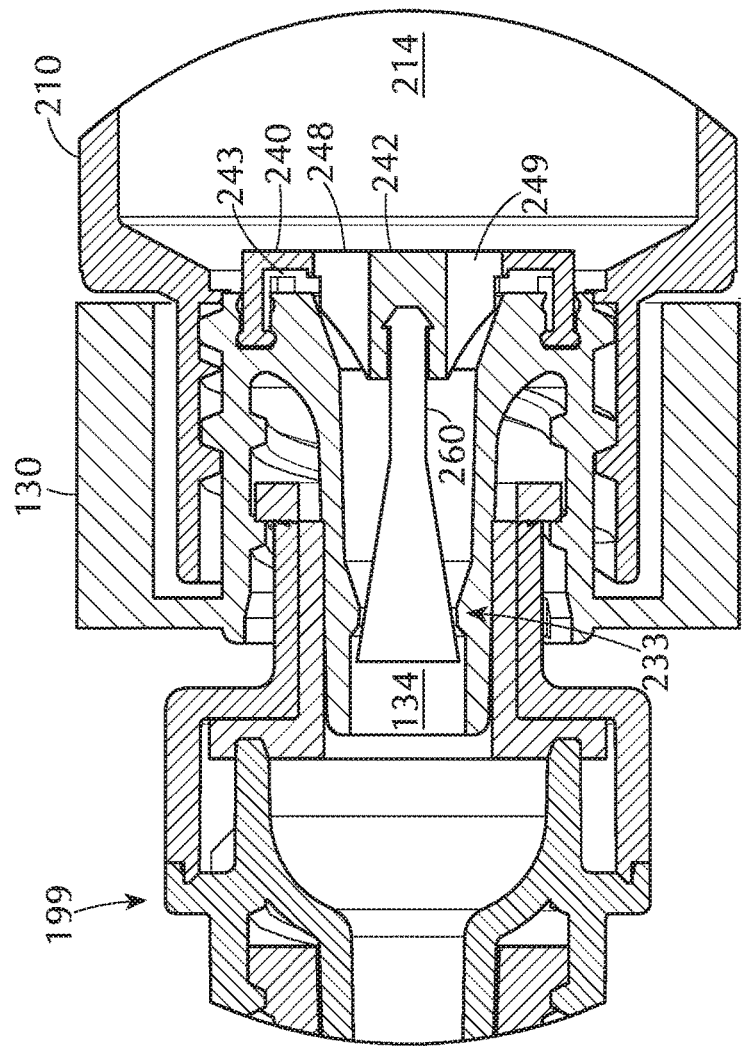
FIG. 34 shows an expanded cross-sectional view of the distal end of the syringe assembly of FIG. 33.
Figure 35:
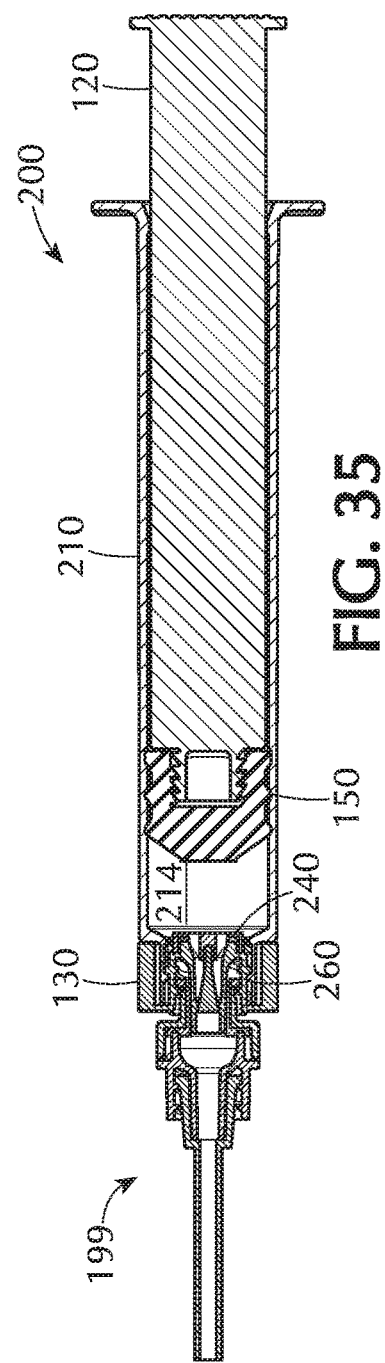
FIG. 35 shows a cross-sectional side view of a syringe assembly of FIG. 33 with the plunger being drawn proximally in accordance with one or more embodiments of the invention.
Figure 36:
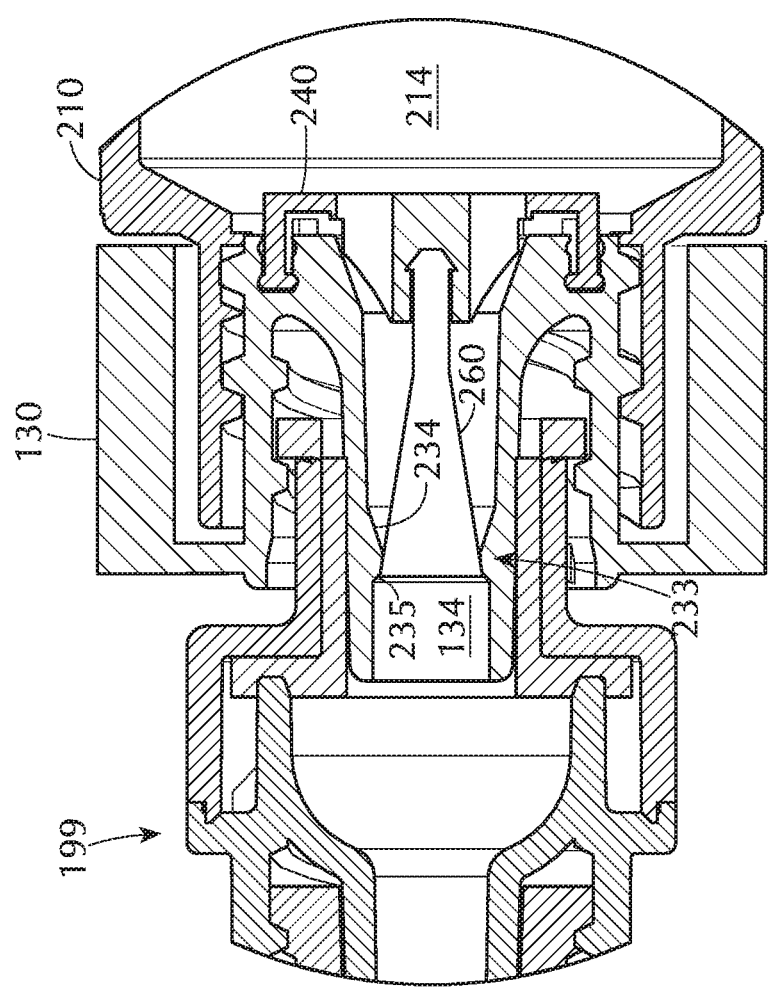
FIG. 36 shows an expanded cross-sectional view of the distal end of the syringe assembly of FIG. 35.

In another embodiment, shown in FIGS. 33 and 34, the valve stem 260 is positioned to extend from the proximal side of the valve seat 233 to the distal side of the valve seat 233. The distal end 262 of the valve stem 260, which is the larger diameter end, is on the distal side of the valve seat 233 so that proximal movement of the valve stem 260 causes the valve stem 260 to form a fluid-tight seal with the valve seat 233. In one or more embodiments, when distally directed force is applied to the stopper 150 (which can be through movement of the plunger rod 120), the valve stem 260 is not in complete contact with the valve seat 233. This can be seen in FIG. 34. Fluid can flow from the chamber 214 through the openings 248 in the proximal face 241 of the valve 240 (if openings 248 are present) along the channels 249 (if present), around the valve stem 260, passing between the valve stem 260 and the valve seat 233 toward the vascular access device.

When a proximally directed force, or no force, is applied to the stopper (which can be through movement of the plunger rod 120), the valve stem 260 is in complete contact with the valve seat 233 to form a fluid-tight seal which isolates the chamber from the cap 130 and vascular access device 199. This can be seen in FIGS. 35 and 36. Referring to the expanded view of FIG. 36, the valve stem 260 rests against the distal ramp 235 of the valve seat 233 forming the fluid-tight seal.

In some embodiments, the cap 130 comprises a valve seat 233 within the passageway 134. The valve seat 233 is biased radially inwardly and has a proximal ramped face and a distal ramped face. The distal end 262 of the valve stem 260, in an initial position, is in contact with the proximal ramped face of the valve seat forming a seal against distal fluid movement and the plurality of openings 248 in the valve 240 are unobstructed.

In one or more embodiments, when the valve 240 is in the initial position, proximally directed force on the plunger causes the distal end 262 of the valve stem 260 of move proximally from the proximal face 234 of the valve seat 233 allowing fluid to flow from a vascular access device 199 toward the cap 130 and then into the chamber 214. In some embodiments, subsequent distally directed force on the plunger rod 120 causes the distal end 262 of the valve stem 260 to pass from a proximal side of the valve seat 233 to a distal side of the valve seat 233. This moves the valve 240 from the open position allowing fluid communication between the cap and the chamber through the plurality of openings in the valve to the closed position preventing fluid communication between the cap and the chamber.

In some embodiments, when distally directed force is applied to the stopper 150, the valve stem 260 is not in complete contact with the valve seat 233. When a proximally directed force or no-force is applied to the stopper 150, the distal end 262 of valve stem 260 is in complete contact with the distal ramp 235 of valve seat 233 to form a fluid-tight seal isolating the chamber from the vascular access device 199.

Figure 37:
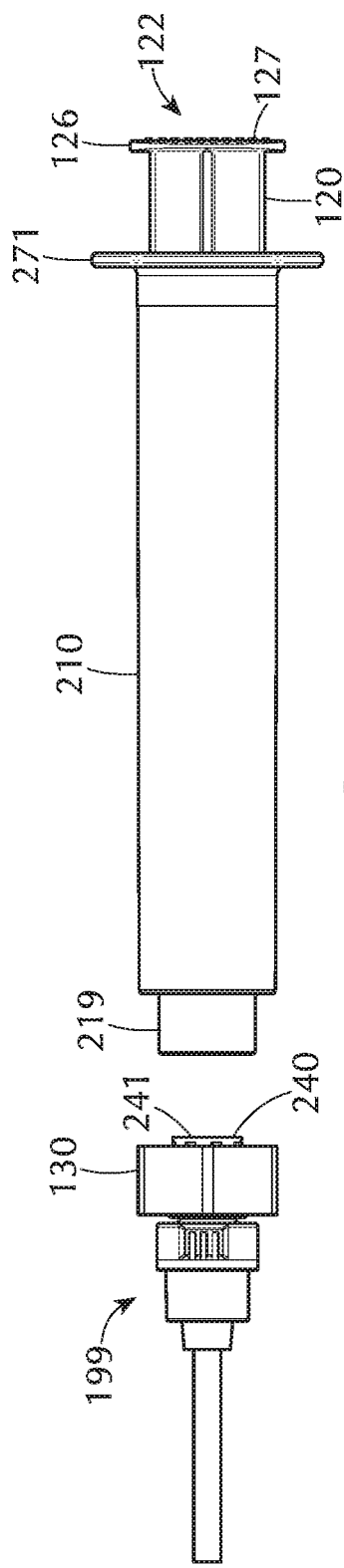
FIG. 37 shows a side view of a syringe assembly with the vascular access device, cap and valve removed in accordance with one or more embodiments of the invention.
Figure 38:
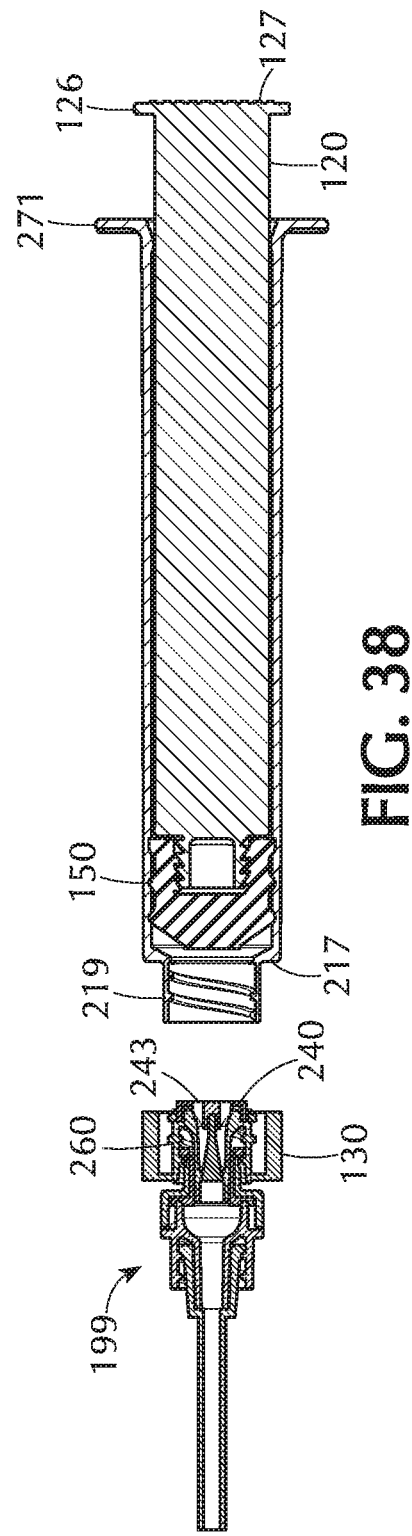
FIG. 38 shows a cross-sectional view of the syringe assembly of FIG. 37.
Figure 39:
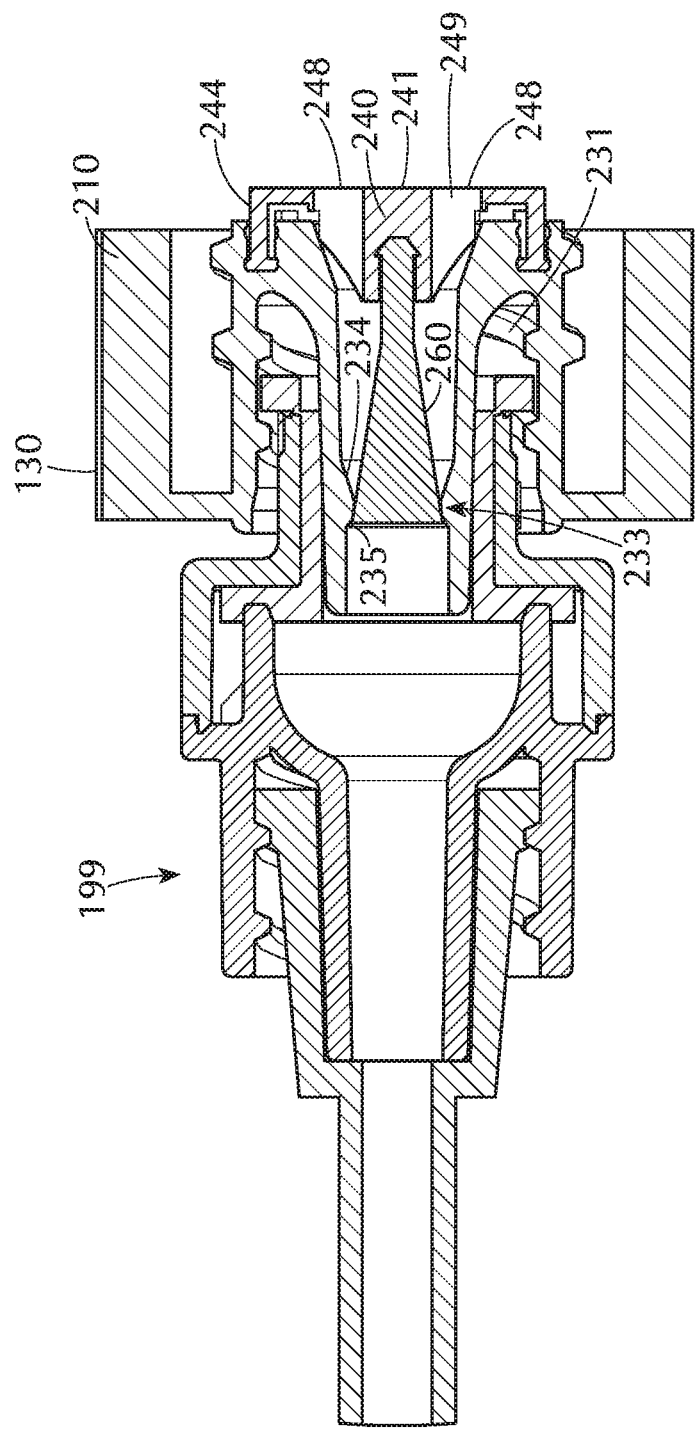
FIG. 39 shows an expanded cross-sectional view of the vascular access device and valve of FIG. 38.

Referring to FIGS. 37-39, after the valve 240 is moved into the closed position, the cap 130 and vascular access device 199 are isolated. The barrel 210 can be removed from the cap 130 leaving the cap 130, valve 240 and valve stem 260 attached to the vascular access device 199, thereby sealing the VAD from contamination. It can be seen from FIG. 39 that the openings 248 in the proximal face 241 are unblocked. However, the fluid-tight seal formed by the valve stem 260 in contact with the valve seat 233 prevents fluid from moving from the vascular access device (i.e., reflux) or contamination of the vascular access device 199.

Figure 40:
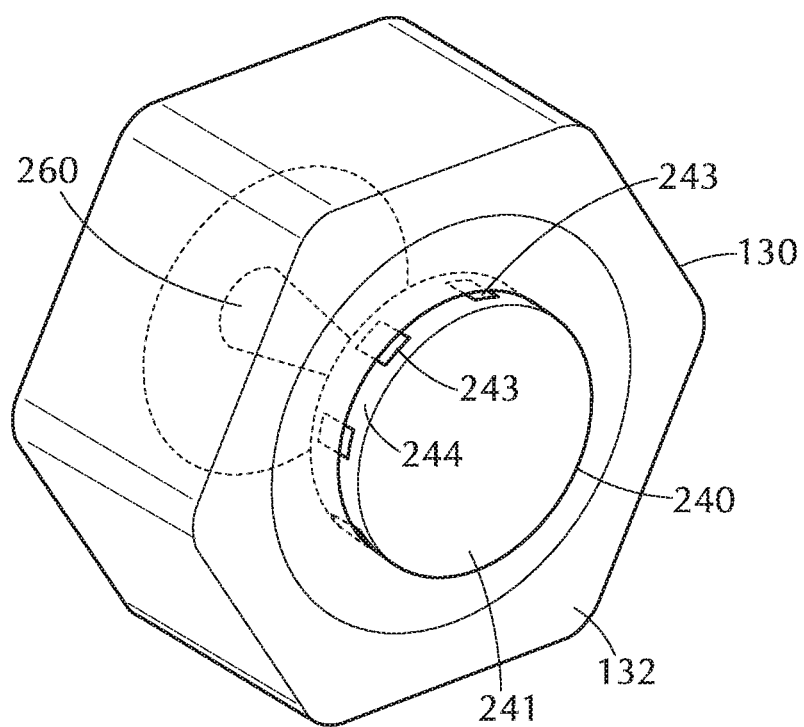
FIG. 40 shows a proximal view of a cap and valve in accordance with one or more embodiments of the invention.

FIG. 40 shows another embodiment of the cap 130, valve 240 and valve stem 260 combination in a closed position. It can be seen that the plurality of openings 243 in the sidewall 244 of the valve 240 are partially unblocked. To close the device and prevent reflux and contamination, although not shown, the valve stem 260 would be in contact with the valve seat 233 in the passageway of the cap 130, similar to that of FIG. 39.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A flush syringe assembly comprising:
a barrel including a side wall having an inside surface defining a chamber for retaining fluid, an outside surface, an open proximal end, a distal end including a distal wall having an aperture therethrough in fluid communication with the chamber;
an elongate plunger rod disposed within the barrel, the elongate plunger rod comprising a distal end including a stopper slidably positioned in fluid-tight contact with the inside surface of the barrel so that distal movement of the stopper relative to the barrel pushes fluid out of the barrel;
a cap comprising a passageway therethrough in fluid communication with the chamber, the cap including a Luer connector on a distal end and being releasably connectable to a vascular access device (VAD) and a proximal end releasably attachable to the barrel;
a sleeve coaxial with the barrel and having a distal end and a proximal end, and an inside surface and an outside surface;
a hub connected to the distal end of the sleeve and having a distal face and a proximal face adjacent to the distal end of the cap;
a disinfecting system comprising a disinfectant in contact with the distal face of the hub, wherein the sleeve slides from a distal position in which the proximal face of the hub conceals the distal end of the cap to a proximal position which the disinfectant system is released by contact with the distal end of the cap upon proximal motion of the sleeve; and
a gasket disposed at the distal end of the barrel between the cap and the distal wall of the barrel.

2. The flush syringe assembly of claim 1, wherein the gasket is made of rubber or plastic.

3. The flush syringe assembly of claim 1, wherein the sleeve further comprises one or more cutouts to provide visibility to contents of the barrel.

4. The flush syringe assembly of claim 1, wherein the outside surface of the barrel further comprises two annular positioning ridges, a distal annular positioning ridge and a proximal annular positioning ridge.

5. The flush syringe assembly of claim 4, wherein the inside surface of the sleeve further comprises two annular positioning grooves for controlling a position of the sleeve relative to the barrel by engaging with the annular positioning ridges on the outside surface of the barrel.

6. The flush syringe assembly of claim 4, wherein the gasket has an outer diameter equal to the outer diameter of the barrel at the annular positioning ridges.

7. The flush syringe assembly of claim 1, wherein the distal end of the sleeve is connected to the disinfecting system by an interference fit.

8. The flush syringe assembly of claim 1, wherein the disinfecting system further comprises a removable cover for protecting the disinfecting system prior to use and a disinfectant-carrying medium.

9. The flush syringe assembly of claim 1, wherein the stopper is made of material selected from the group consisting of thermoplastic elastomers, natural rubber, synthetic rubber, thermoplastic materials and combinations thereof.

10. The flush syringe assembly of claim 1, further comprising a valve comprising a plug positioned adjacent to the distal end of the barrel and in contact with the proximal end of the cap.

11. The flush syringe assembly of claim 10, wherein the plug having a proximal face and a sidewall extending distally therefrom, the sidewall including a plurality of openings that allow fluid communication between the chamber and the VAD.

12. The flush syringe assembly of claim 11, wherein the valve being movable by distally directed force applied by the stopper from a proximal open position that permits fluid flow between the chamber and the VAD through the plurality of openings and a distal closed position that prevents fluid communication between a blood vessel and the VAD.

13. The flush syringe assembly of claim 1, wherein the cap engages with the VAD by one or more of threads that engage with complementary threads on the VAD or an interference fit.

14. A flush syringe assembly comprising:
a barrel including a side wall having an inside surface defining a chamber for retaining fluid, an outside surface, an open proximal end, a distal end including a distal wall having an aperture therethrough in fluid communication with the chamber;
an elongate plunger rod disposed within the barrel, the elongate plunger rod comprising a distal end including a stopper slidably positioned in fluid-tight contact with the inside surface of the barrel so that distal movement of the stopper relative to the barrel pushes fluid out of the barrel; and
a valve having a distal end and a proximal end, the valve having a proximal face and a sidewall extending distally therefrom, a central portion of the distal end of the valve having a projection, wherein the proximal face of the valve comprises a plurality of openings allowing fluid communication between the chamber and the aperture, the plurality of openings extend along a length of the projection as a series of channels, the plurality of openings have a hexagonal shape at the proximal face of the valve and the series of channels have a circular shape along the length of the series of channels.

15. The flush syringe assembly of claim 14, further comprising a cap having a passageway therethrough in fluid communication with the chamber.

16. The flush syringe assembly of claim 15, wherein the cap includes a Luer connector on a distal end being releasably connectable to a vascular access device (VAD) and a proximal end releasably attachable to the barrel.

17. A flush syringe assembly comprising:
a barrel including a side wall having an inside surface defining a chamber for retaining fluid, and outside surface, an open proximal end, a distal end including a distal wall having an aperture therethrough in fluid communication with the chamber;
an elongate plunger rod disposed within the barrel, the elongate plunger rod comprising a distal end including a stopper slidably positioned in fluid-tight contact with the inside surface of the barrel so that distal movement of the stopper relative to the barrel pushes fluid out of the barrel; and a valve having a distal end and a proximal end, the valve having a proximal face and a sidewall extending distally therefrom, a central portion of the distal end of the valve having a projection, wherein the proximal face of the valve comprises a plurality of openings allowing fluid communication between the chamber and the aperture, the plurality of openings extend along a length of the projection as a series of channels, wherein the projection is frustoconically shaped.

* * * * *